United States Patent
Giliyar et al.

(10) Patent No.: US 9,107,921 B2
(45) Date of Patent: Aug. 18, 2015

(54) ORAL DOSAGE FORMS FOR OXYGEN CONTAINING ACTIVE AGENTS AND OXYL-CONTAINING POLYMERS

(71) Applicants: Chandrashekar Giliyar, North Maple Grove, MN (US); Satish Kumar Nachaegari, Salt Lake City, UT (US); Chidambaram Machiappan, Salt Lake City, UT (US); Mahesh V. Patel, Salt Lake City, UT (US); Srinivasan Venkateshwaran, Salt Lake City, UT (US)

(72) Inventors: Chandrashekar Giliyar, North Maple Grove, MN (US); Satish Kumar Nachaegari, Salt Lake City, UT (US); Chidambaram Machiappan, Salt Lake City, UT (US); Mahesh V. Patel, Salt Lake City, UT (US); Srinivasan Venkateshwaran, Salt Lake City, UT (US)

(73) Assignee: Spriaso LLC, Salt Lake City, UT (US)

(*) Notice: Subject to any disclaimer, the term of this patent is extended or adjusted under 35 U.S.C. 154(b) by 0 days.

(21) Appl. No.: 14/555,043

(22) Filed: Nov. 26, 2014

(65) Prior Publication Data

US 2015/0087666 A1 Mar. 26, 2015

Related U.S. Application Data

(63) Continuation of application No. 13/342,883, filed on Jan. 3, 2012.

(51) Int. Cl.
| | |
|---|---|
| A61K 31/485 | (2006.01) |
| A61K 31/194 | (2006.01) |
| A61K 31/4402 | (2006.01) |
| A61K 45/06 | (2006.01) |
| A61K 31/09 | (2006.01) |
| A61K 31/137 | (2006.01) |
| A61K 9/20 | (2006.01) |

(52) U.S. Cl.
CPC ............. *A61K 31/485* (2013.01); *A61K 9/2054* (2013.01); *A61K 31/09* (2013.01); *A61K 31/137* (2013.01); *A61K 31/194* (2013.01); *A61K 31/4402* (2013.01); *A61K 45/06* (2013.01)

(58) Field of Classification Search
CPC ... A61K 31/485; A61K 9/2054; A61K 45/06; A61K 31/09; A61K 31/137; A61K 31/4402; A61K 31/194; A61K 2300/00
See application file for complete search history.

(56) References Cited

U.S. PATENT DOCUMENTS

| | | | |
|---|---|---|---|
| 6,372,252 B1 | 4/2002 | Blume et al. | |
| 6,955,821 B2 | 10/2005 | Davis et al. | |
| 7,838,032 B2 | 11/2010 | Davis et al. | |
| 2005/0232987 A1* | 10/2005 | Srinivasan et al. | ............ 424/464 |

OTHER PUBLICATIONS

Bernthal et al.; A New, Low Viscosity, Direct Compression Grade HYpromellose for Controlled Release Applications; Poster presented a the 2009 Annual Meeting and Exposition of the American Association of Pharmaceutical Scientists; Nov. 8-12, 2009; 4 pages; Dow Wolff Cellulosics R&D, The Dow Chemical Company, Midland, Michigan.

Cder, US FDA, http://www.fda.gov/ohrms/dockets/ac/07/briefing/2007-4323b1-02-fda.pdf, accessed on Jan. 14, 2014. Table 3, Sale of combination OTC cough/cold products by dosage form from year 2002 through 2006, row: chlorpheniramine/systemic oral solid L/A; p. 291. Table 5, Total number of dispensed prescriptions for cough/cold products in the pediatric age group 0-6 years for years 2002-2006, row: chlorpheniramine combo; p. 294.

Crutcher JE, Kantner TR. The effectiveness of antihistamines in the common cold. *J Clin Pharmacol*. Jan. 1981;21(1):9-15.

Doyle WJ, McBride TP, Skoner DP, Maddern BR, Gwaltney JM, Jr, Uhrin M. A double-blind, placebo-controlled clinical trial of the effect of chlorpheniramine on the response of the nasal airway, middle ear and eustachian tube to provocative rhinovirus challenge. *Pediatr Infect Dis J*. Mar. 1988;7(3):229-38.

Eddy NB, Friebel H, Hahn KJ, Halbach H. Codeine and its alternative for pain and cough relief: 3. The antitussive action of codeine—mechanism, methodology and evaluation. *Bull Wld Hlth Org*. 1969;40(3):425-54.

Hagen NA. An approach to cough in cancer patients. *J Pain Symptom Manage*. May 1991;6(4):257-62.

Hennies H., Friderichs E., and Schneider J. *Receptor binding, analgesic and antitussive potency of tramadol and other selected opioids*. Arzneimittel-Forschung 1988; 38(7):877-880.

Homsi J, Walsh D, Nelson KA. Important drugs for cough in advanced cancer. *Supp Care Cancer*. 2001;9(8):565-74.

Howard JC, Jr, Kantner TR, Lilienfield LS, et al. Effectiveness of antihistamines in the symptomatic management of the common cold. *JAMA*. Nov. 30, 1979;242(22):2414-7.

Palangio M, Widerman GL, Keffer M, et al. *Dose-response effect of combination hydrocodone with ibuprofen in patients with moderate to severe postoperative pain*. Clin Ther. 2000; 22(8):990-1002.

(Continued)

*Primary Examiner* — Johann R Richter
*Assistant Examiner* — Genevieve S Alley
(74) *Attorney, Agent, or Firm* — Thorpe North & Western, LLP

(57) ABSTRACT

A pharmaceutical tablet for oral administration once every 12 hours is provided. The tablet includes a first active agent that is a tri-oxy active agent, a second active agent, and a release rate controlling non-ionic oxyl-containing hydrophilic polymer. The tablet is a matrix tablet and a single-dose administration of one or more tablets to a subject under fasted conditions provides a mean Cm~ for each of the first active agent and the second active agent that is 70% to 135% of a respective mean Cm~ provided by administering an immediate release oral dosage form to a subject under fasted conditions every 4 to 6 hours over a 12 hour time period, wherein cumulative dosage amounts administered over the 12 hour time period of each active agent is equivalent to the respective amount of each active agent in the pharmaceutical tablet.

22 Claims, 3 Drawing Sheets

(56) References Cited

OTHER PUBLICATIONS

Reisine T, Pasternak G. Chapter 23; Opioid analgesics and antagonists. In: Hardman JG, Limbird LE, eds. *Goodman and Gilman's the Pharmacological Basis of Therapeutics*, 9th ed. McGraw-Hill. New York,NY 1996:521-555.

US FDA, Code of Federal Regulations Title 21. http://www.accessdata.fda.gov/scripts/cdrh/cfdocs/cfcfr/cfrsearch.cfm?fr=341.74. Labeling of antitussive drug products; 21 CFR 341.74; Revised as of Apr. 1, 2013; accessed on Jan. 14, 2014.

US FDA, Code of Federal Regulations Title 21. http://www.accessdata.fda.gov/scripts/cdrh/cfdoc/cfcfr/cfrsearch.cfm?fr=341.72. Labeling of antihistamine drug product; 21 CFR 341.72; Revised as of Apr. 1, 2013; accessed on Jan. 14, 2014.

US FDA, Code of Federal Regulations Title 21. http://www.accessdata.fda.gov/scripts/cdrh/cfdocs/cfcfr/cfrsearch.cfm?fr=341.14. Cold, Cough, Allergy, Bronchodilator, and Antiasthmatic Drug Products for Over-The-Counter Human Use, Active Ingredients, Antitussive Active Ingredients, Revised as of Apr. 1, 2013; accessed on Jan. 14, 2014.

US FDA, Code of Federal Regulations Title 21 http://www.accessdata.fda.gov/scripts/cdrh/cfdocs/cfcfr/cfrsearch.cfm?fr=341.12. Cold, Cough, Allergy, Bronchodilator, and Antiasthmatic Drug Products for Over-The-Counter Human Use, Active Ingredients, Antihistamine Active Ingredients, Revised as of Apr. 1, 2013; accessed on Jan. 14, 2014.

US FDA, Code of Federal Regulations Title 21 http://www.accessdata.fda.gov/scripts/cdrh/cfdocs/cfcfr/cfrsearch.cfm?fr=341.70. Cold, Cough, Allergy, Bronchodilator, and Antiasthmatic Drug Products for Over-The-Counter Human Use, Labeling, Revised as of Apr. 1, 2013; accessed on Jan. 14, 2014.

US FDA, Code of Federal Regulations Title 21. http://www.accessdata.fda.gov/scripts/cdrh/cfdocs/cfcfr/cfrsearch.cfm?fr=341.40. Permitted combinations of active ingredients; 21 CFR 341.40; Revised as of Apr. 1, 2013; accessed on Jan. 14, 2014.

CODEPREX PENNKINETIC Product Label; UCB Manufacturing Inc; Revised Jul. 2013.

ZODRYL AC 50- COD-CPM-IR Product label; CodaDose, Inc.; Revised Aug. 2009.

Rumore, Martha M.; *Clinical Pharmacokinetics of Chlorpheniramine*; Drug Intelligence and Clinical Pharmacy; Sep. 1984; vol. 18; pp. 701-707.

U.S. Appl. No. 14/194,620, filed Feb. 28, 2014; Chandrashekar Gilyar; office action dated May 6, 2014.

U.S. Appl. No. 14/194,620, filed Feb. 28, 2014; Chandrashekar Giliyar; office action dated Sep. 9, 2014.

Dow; Using METHOCEL Cellulose Ethers for Controlled Release of Drugs in Hydrophilic Matrix Systems; Dow Chemical Brochure; Jul. 2000; 36 pages; The Dow Chemical Company.

U.S. Appl. No. 13/342,883, filed Jan. 3, 2012; Chandrashekar Giliyar; office action dated Feb. 4, 2015.

\* cited by examiner

ORAL DOSAGE FORMS FOR OXYGEN CONTAINING ACTIVE AGENTS AND OXYL-CONTAINING POLYMERS

This application is a continuation of U.S. patent application Ser. No. 13/342,883, filed Jan. 3, 2012, which is herein incorporated by reference.

FIELD OF THE INVENTION

The present invention relates to oral dosage forms containing combination of pharmaceutical active agents for treating cough and associated methods of treatment and manufacture. Accordingly, this invention involves the fields of chemistry, pharmaceutical sciences, medicine and other health sciences.

BACKGROUND OF THE INVENTION

Tri-oxy active agents (drugs having at least three different oxygen-containing groups) such as guaifenesin, codeine and hydrocodone are used to treat cold and cough as well as other related symptoms. Often, cold, cough, allergies, and other similar conditions can require treatment with multiple active agents in order to simultaneously alleviate multiple symptoms. For example, combinations of active agents such as codeine or hydrocodone with a mucolytic or a decongestant or an anti-tussive have been used for management of cold, cough and flu symptoms. However, these combinations are primarily available as inconvenient liquids which are prone to dosing errors and which require frequent dosing in order to provide consistent and continuous symptom relief. Commercially available combination products tend to be short-acting and often require dosing every four, six or eight hours. The need for frequent dosing and the re-emergence of symptoms between doses often make sleeping difficult, which in turn can delay the recovery process. Moreover, the combination dosage forms must meet each active agent's own unique pharmacokinetic requirement for symptom or co-symptom relief.

Guaifenesin (glyceryl guaiacolate, GGE) is a widely used expectorant that assists in loosening phlegm (mucus) and thins bronchial secretions to make cough more productive. The structure of guaifenesin is generally shown as:

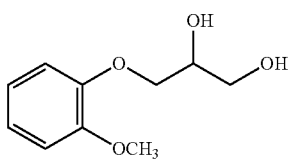

Guaifenesin
($C_{10}H_{14}O_4$; Molecular Weight: 198.22)

Guaifenesin is thought to act by increasing the volume and reducing the viscosity of secretions in the trachea and bronchi. It is also reported to stimulate the flow of respiratory tract secretions allowing ciliary movement to carry the loosened secretions upward toward the pharynx. Guaifenesin has a plasma half-life of about one hour. GGE is commonly available as an immediate release tablet (200 mg and 400 mg strengths) requiring frequent dosing such as once every four hours.

Codeine (3-methylmorphine) is an opiate used widely for its antitussive (cough suppression) and analgesic properties. Its structure is generally shown as:

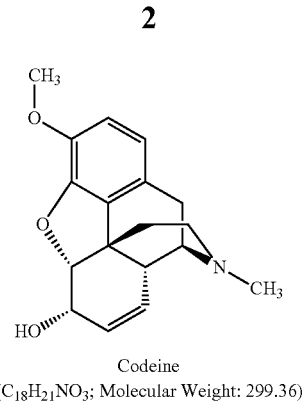

Codeine
($C_{18}H_{21}NO_3$; Molecular Weight: 299.36)

Codeine helps in temporary control of cough caused by minor throat and bronchial irritation as occurs with common cold or inhaled irritants. The recommended antitussive codeine dose in adults and children 12 years of age and above is 10 to 20 mg codeine administered every 4 to 6 hours not to exceed 120 mg/day. The reported a plasma half-life for codeine is about 2.5-3 hours. It is more commonly available as immediate release dosage form that requires frequent dosing.

Hydrocodone is a narcotic pain reliever and a cough suppressant and its structure is generally shown as:

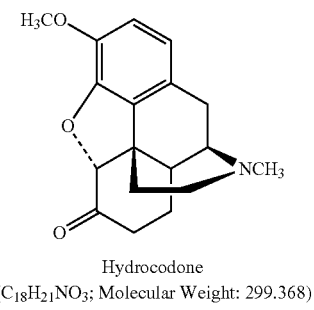

Hydrocodone
($C_{18}H_{21}NO_3$; Molecular Weight: 299.368)

Hydrocodone is an opioid derived from codeine and is recognized as both an effective analgesic and antitussive agent. It is generally considered to be one of the potent and effective antitussive drugs and is believed to act, at least in part, by a direct depressant effect on a cough center in the medulla and to a lesser degree the respiratory center. The recommended adult hydrocodone bitartrate dosage for the symptomatic relief of cough is 5 mg (as hydrocodone bitartrate) every 4 to 6 hours as needed, not to exceed 30 mg in 24 hours. Children 6 to 12 years of age should be administered ½ the adult dose, not to exceed a total of 15 mg drug in 24 hours. It is reported to have a plasma half-life of about 3.8 to 6 hours. It is more commonly available as immediate release dosage form that requires frequent dosing.

Pseudoephedrine is a sympathomimetic drug of the phenethylamine and amphetamine chemical classes. It is found as a hydrochloride or sulfate salt in many over-the-counter preparations more commonly as a single ingredient formulation. It is generally indicated for temporary relief of nasal and/or sinus congestion due to the common cold, hay fever or other upper respiratory allergies. The typical dose for adults and children 12 years of age is 60 mg to 120 mg.

Chlorpheniramine is a propylamine antihistamine ($H_1$-receptor antagonist) that also possesses anticholinergic and sedative activity. It prevents released histamine from dilating capillaries and causing edema of the respiratory mucosa.

Chlorpheniramine maleate is commonly available in immediate release dosages as an over-the-counter anti-allergy drug. Following oral administration of chlorpheniramine the peak plasma concentration is reached in 2-3 hours and its duration of effect lasts for 4-6 hours, therefore requiring frequent dosing. The oral dose in adults and children 12 years of age and older is typically 4 mg chlorpheniramine maleate every 4 to 6 hours.

Dextromethorphan hydrobromide monohydrate ($C_{18}H_{25}NO \cdot HBr \cdot H_2O$) is a centrally acting antitussive agent which elevates the threshold for coughing. It has no analgesic or addictive properties. Its dose is 10 to 30 mg every 4 to 8 hours. Dextromethorphan exerts its effect in 15 to 30 minutes after oral administration and its duration of action is for approximately three to six hours, hence requiring frequent dosing.

Phenylephrine is a potent decongestant agent commonly used for temporary relief of nasal congestion associated with allergy or head colds symptoms, etc. Following oral administration, phenylephrine exerts its effect in 15 to 30 minutes and its effect persists for up to 4 hours, therefore requiring frequent dosing. The usual adult dose of phenylephrine is 10 to 20 mg orally every 4 hours as needed.

Most long acting oral dosage forms currently available to treat the above-recited conditions contain only one active agent, and typically require coating or bi-layering to enable various controlled or sustained release including biphasic release of the active.

Oxyl-containing polymers (having oxygen-containing groups) such as methacrylates, carbomers, hypromellose (HPMC), etc. have been used to enable slow release dosage forms having a single tri-oxy or non-tri-oxy active. As reported for a single-layer matrix tablet of a non-tri-oxy active such as chlorpheniramine, an HPMC polymer (Methocel K4M) to active ratio of about 1:1 provides a time to 50% in vitro drug release of about 3.5 hours. However, such very slow release profile is unsuitable for a 12 hour dosing therapy of tri-oxy actives to allow sleeping through the night and without excessive daytime grogginess.

Use of oxyl-containing non-ionic hydrophilic polymers (e.g. HPMC) have also been reported to formulate a single di-oxy active (having two different oxygen-containing groups) such as propranolol HCl into a matrix tablet, wherein a HPMC (Methocel K4M) to active agent ratio is 1:0.3 by weight, and which provides a time to 50% drug release in vitro of about 4 hours. However, such a slow release profiles for tri-oxy actives is unsuitable for a 12 hour dosing therapy.

Due to tremendous safety liability associated with deviations from acceptable peak blood concentrations, many tri-oxy active agents, such as narcotics like codeine and hydrocodone, require stable blood levels upon oral dosing. For a solid dosage form (tablet, capsules etc.) containing multiple actives with a hydrophilic polymer, the design and management of the dosage form performance for a given intended use becomes increasingly challenging. This is especially true with regards to efficacy, release, and pharmacokinetic requirements, which can be further complicated for each active due to its distinct physiochemical and biological properties. Additionally, food interactions with an oral dosage form upon ingestion can produce unacceptable higher blood concentrations of actives, especially from a longer acting product which has higher active strength per dosage unit relative to an immediate release dosage form. It is noteworthy that regulatory concerns related to food effects of a bilayer tablet containing ionic polymer of guaifenesin and codeine have been reported in the literature.

To date, there appear to be no known teachings that enable a combination matrix tablet containing at least one tri-oxy active, such as guaifenesin or a codone, that upon single administration of the combination tablet of two pharmacologically different actives are released in an optimal manner, individually and collectively, and that enables optimal blood levels of each active as required for twice-a-day dosing therapy for regulatory approval purposes.

SUMMARY OF THE INVENTION

The present inventors have recognized a benefit to providing a tri-oxy active containing pharmaceutical tablet that is a matrix tablet formulated for dosage every twelve hour and which does not have negative food effects. Moreover, it has been surprisingly found that by including certain levels of at least one tri-oxy active agent in an oxyl-containing non-ionic hydrophilic polymer based matrix tablet, there exists a unique optimal oxyl content composition that enables a 12 hour product having no food effect.

Accordingly, the present disclosure is drawn to combination pharmaceutical solid dosage forms comprising at least one tri-oxy active agent, a second active agent, and optionally, a third active agent. The dosage form is formulated for oral dosing once every 12 hours. The tablet can include a first active agent that is a tri-oxy active agent, a second active agent, and a release rate controlling non-ionic oxyl-containing hydrophilic polymer. The total oxyl content of the hydrophilic polymer in the tablet is from about $4 \times 10^{-4}$ moles to about $2.0 \times 10^{-3}$ moles. In one embodiment, a pharmaceutical matrix tablet for oral administration once every 12 hours is provided. Related methods of use and treatment are also provided. In one aspect, a single-dose administration of one or more tablets to a subject under fasted conditions can provide a mean $C_{max}$ for each of the first active agent and the second active agent that is about 70% to about 135% of a respective mean $C_{max}$ provided by administering an immediate release oral dosage, as a combination or respective single active dosage form, to a subject under fasted conditions every 4 to 6 hours over a 12 hour time period, wherein cumulative dosage amounts administered over the 12 hour time period of each active agent from the immediate release dosage forms are equivalent to the respective amount of each active agent in the pharmaceutical tablet.

In another embodiment, a combination pharmaceutical solid dosage forms is provided that includes at least one tri-oxy active agent, a second active agent, and optionally, an third active agent. The dosage form is formulated for oral dosing once every 12 hours. The tablet can include a first active agent that is a tri-oxy active agent, a second active agent, and a release rate controlling non-ionic oxyl-containing hydrophilic polymer. The total oxyl content of the hydrophilic polymer in the tablet is from about $4 \times 10^{-4}$ moles to about $2.0 \times 10^{-3}$ moles. In one embodiment, a pharmaceutical matrix tablet for oral administration once every 12 hours is provided. Related methods of use and treatment are also provided. In one aspect, a single-dose administration of one or more tablets to a subject under fasted conditions can provide a mean $C_{max}$ for each of the first active agent and the second active agent that is about 70% to about 135% of a respective mean $C_{max}$ provided by administering the same oral dosage to a subject under fed over a 12 hour time period, wherein cumulative dosage amounts administered over a 12 hour time period.

In another embodiment, a pharmaceutical solid dosage form for dosing once every 12 hours is provided. The solid dosage form is a matrix tablet and can include a first active agent that is a tri-oxy active agent, a second active agent, and a release rate controlling non-ionic oxyl-containing hydrophilic polymer. The tablet is formulated such that when placed in a USP Type 2 dissolution apparatus at 50 rpm in 900 mL of 0.1 N hydrochloric acid solution in water at 37° C., about 50 wt % of the first active agent is released in about 1.5 hours to about 3.2 hours. The ratio of the amount of first active released from the tablet to the amount of second active agent released at 1 hour and at 4 hours is between about 0.7:1 and about 1.3:1.

DETAILED DESCRIPTION

Figure 1:
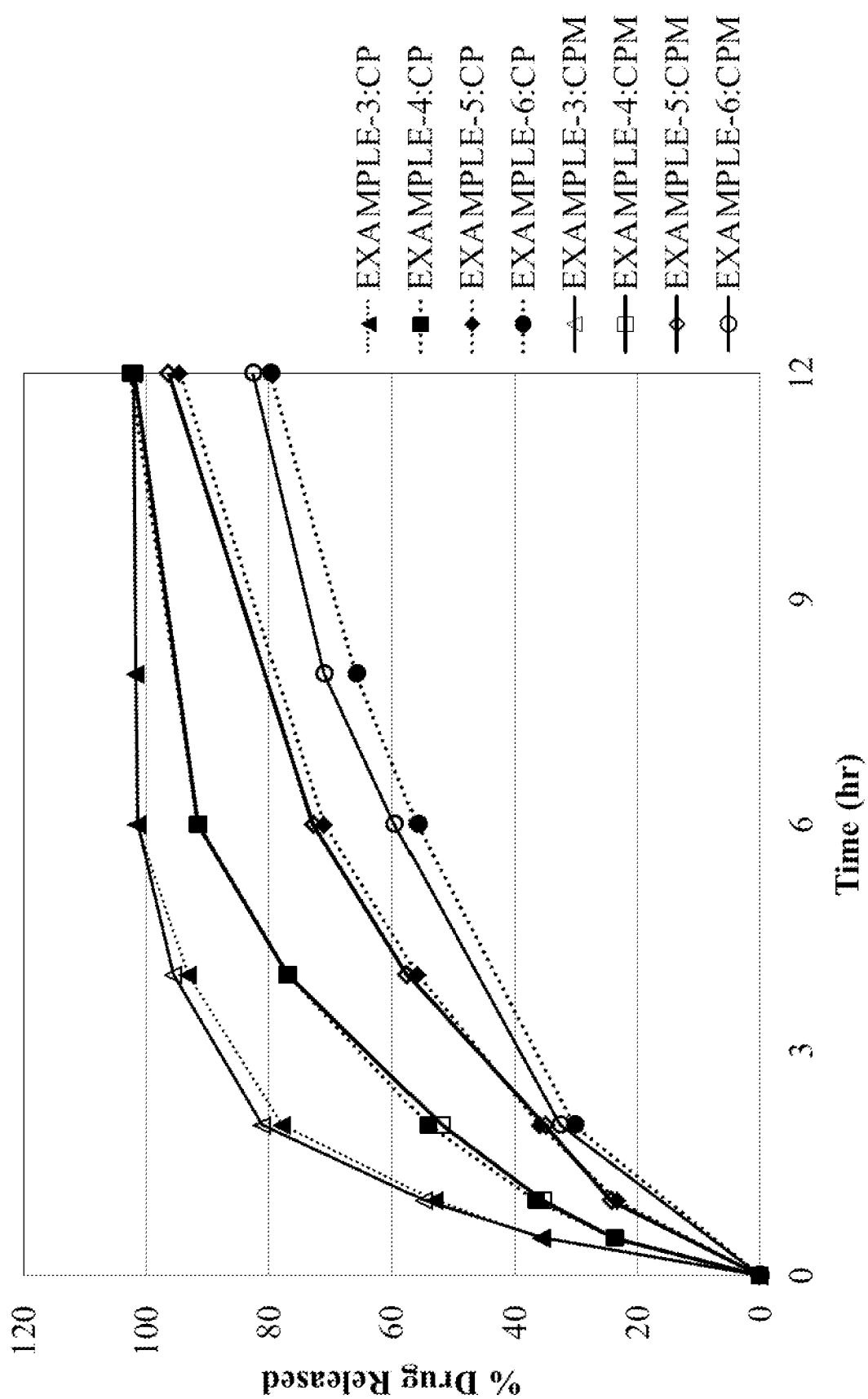
FIG. 1 is a plot of the release profile of several embodiment formulations of the present invention as well as a comparative example.
Figure 2:
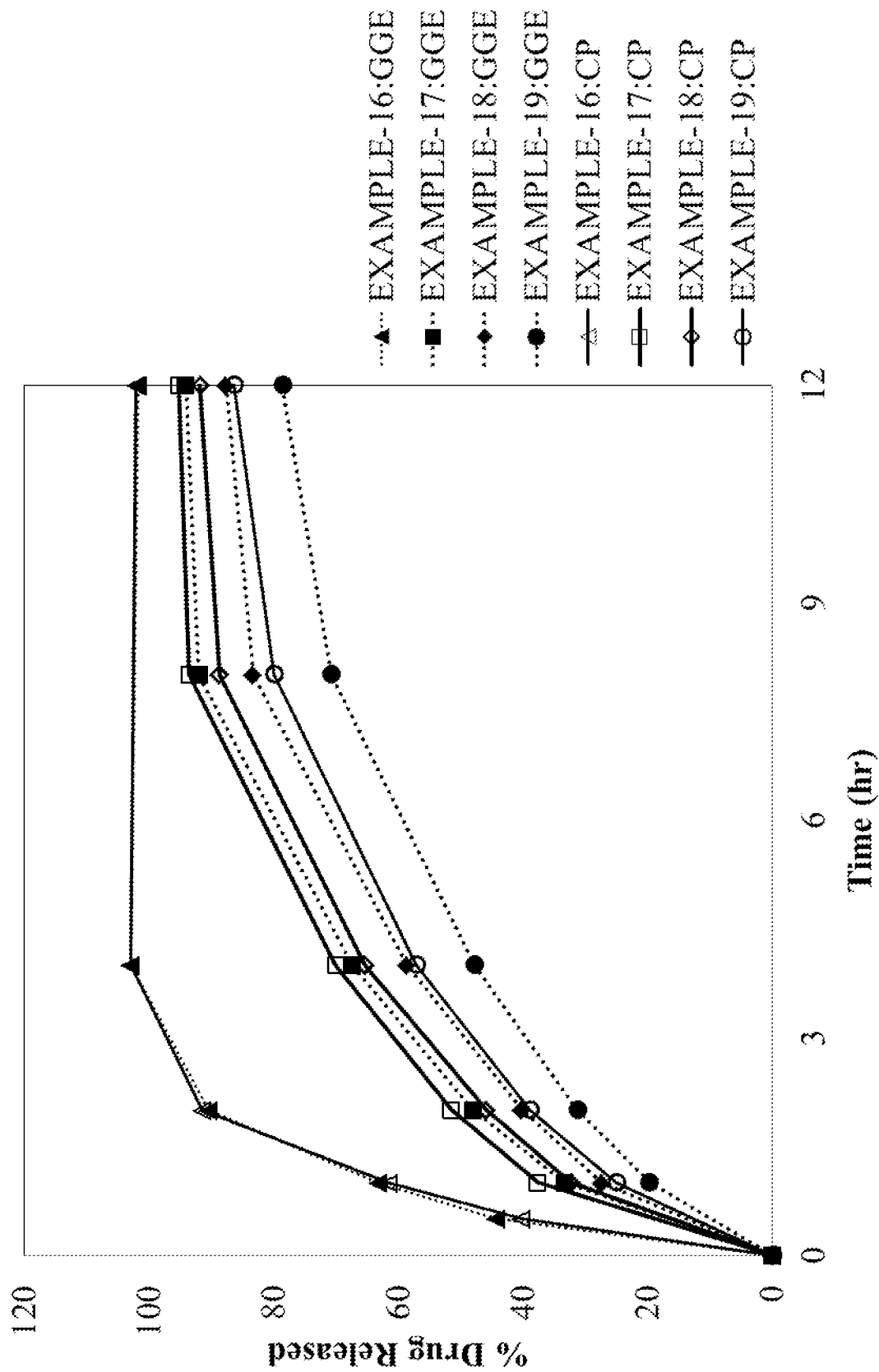
FIG. 2 is a plot release profiles of the actives from some of the representative examples as well as a comparative example.
Figure 3:
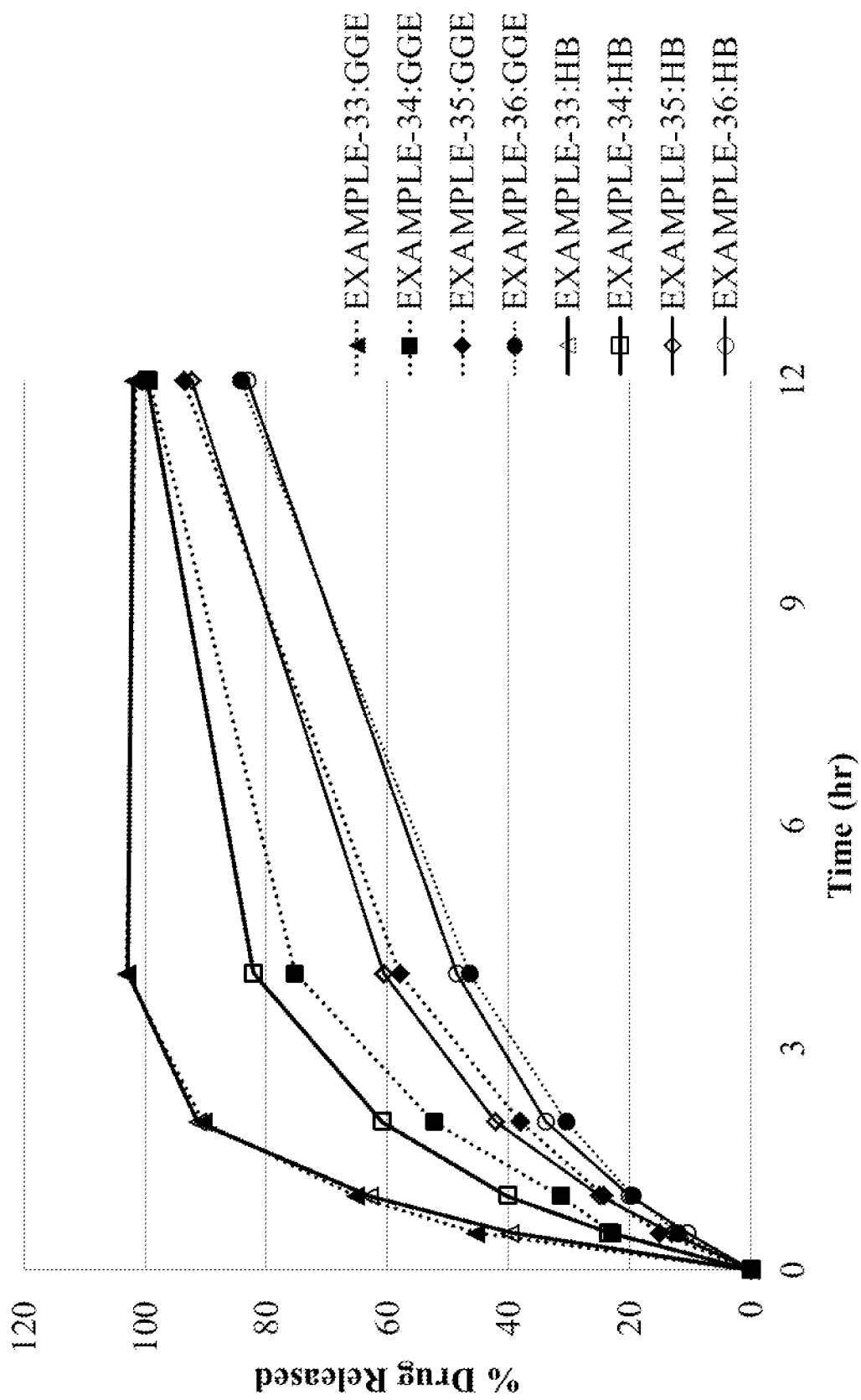
FIG. 3 is a plot of release profiles of the actives from some representative examples and comparative examples.

Before the present pharmaceutical tablets and related methods of use are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

Definitions

As used herein, the term "treatment," when used in conjunction with the administration of oral dosage forms containing guaifenesin and a codone (such as codeine, hydrocodone etc), refers to the administration of the oral dosage forms to subjects who are either asymptomatic or symptomatic. In other words, "treatment" can both be to reduce or eliminate symptoms associated with a condition or it can be prophylactic treatment, i.e. to prevent the occurrence of the symptoms. Such prophylactic treatment can also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Furthermore, the term "dosage form" can include one or more formulation(s) or composition(s) provided in a format for administration to a subject. When any of the above terms is modified by the term "oral" such terms refer to compositions, formulations, or dosage forms formulated and intended for oral administration to subjects.

A temperature processing aid is a compound that, when added to the formulations of the present disclosure, can act to impart handling flexibility with respect to processing temperature.

As used herein, "active agent," "bioactive agent," "pharmaceutically active agent" and "drug" may be used interchangeably to refer to an agent or substance that has measurable specified or selected physiologic activity when administered to a subject in an effective amount. More specifically, as used herein, a "tri-oxy active agent" or "tri-oxy active" has at least three different types of oxygen-containing groups in the "parent" or basic molecular structure. The oxygen-containing group can be a carbonyl or ketone (C=O) group, a methoxy or methoxyl (—OCH$_3$) group, an ether (—O—) group, or hydroxy or hydroxyl (—OH) group. For example, in one embodiment the tri-oxy active can have at least one methoxyl group, at least one ether group, and at least one carbonyl or hydroxyl group.

In one embodiment, the tri-oxy active suitable for this invention is selected from the group comprising guaifenesin, codeine, hydrocodone, guaiacolsulfonate, carbetapentane, methscopolamine, and their pharmaceutical acceptable salts, hydrates, solvates and polymorphs. In a specific embodiment, the tri-oxy active suitable for this invention is selected from the group comprising guaifenesin, codeine, hydrocodone, guaiacolsulfonate and their pharmaceutical acceptable salts, hydrates, solvates and polymorphs.

Similarly, as used herein, a "non-tri-oxy" active agent is a pharmaceutically active agent that contains less than three different oxygen-containing groups. In one embodiment, the non-tri-oxy active can have only one oxygen-containing group. In another embodiment, the non-tri-oxy active does not have any oxygen-containing group.

As used herein, "decongestants" are a class of active agents that induces vasoconstriction of the blood vessels in the nose, throat, and paranasal sinuses, which results in reduced inflammation (swelling) and mucus formation in these areas. These actives are commonly used in the treatment of cough/cold symptoms. Non-limiting examples of suitable decongestants of are ephedrine, levo-methamphetamine, phenylephrine, phenylpropanolamine, propylhexedrine, pseudoephedrine, synephrine, levonordefrin, mephentermine, tuaminoheptane, tymazoline, and their pharmaceutically acceptable salts.

As used herein, the term "non-ionic oxyl-containing hydrophilic polymer" is an uncharged polymer that contains at least hydroxyl (—OH) and methoxyl (—OCH$_3$) groups in its basic monomer structure; the polymer swells/gels and eventually dissolves in water. The number of each of these groups in the polymer determines the rate and extent of its hydration/gelling in an aqueous medium.

Accordingly, the "methoxyl content" or "methoxy content" of the polymer is the total methoxyl groups in the polymer and can be expressed as moles percent (moles %). Similarly, the "hydroxyl content" of the polymer is the total hydroxyl groups in the polymer and can be expressed as moles %. For example, one mole of the Hypromellose 2208, is reported to contain approximately 22 mole % methoxyl groups and 8 mole % hydroxyl groups. In other words, the methoxyl groups and hydroxyl groups constitute about 22% and 8% of the molecular weight, respectively.

As used herein, the "total oxyl content of the polymer" is the sum of the methoxyl and hydroxyl contents in the molecule, and can be expressed in terms of moles. It can also be expressed in terms of moles per dosage unit (example, a tablet), which is calculated based on the amount of that specific polymer present per dosage unit.

The total oxyl content, methoxyl and hydroxyl contents of the non-ionic oxyl-containing hydrophilic cellulose polymer in the tablet of the current invention can be calculated by the following equations:

Total Oxyl Content,
$$\text{in moles} = \left(\frac{\text{Weight of polymer in tablet in grams}}{\text{Molecular Wt of the Polymer}}\right) \times [3 + [Dp*(A+1)]]$$

Total Methoxyl Content,
$$\text{in moles} = \left(\frac{\text{Weight of polymer in dosage form in grams}}{\text{Molecular Wt of the Polymer}}\right) * (D_p * A)$$

Total Hydroxyl Content,
$$\text{in moles} = \left(\frac{\text{Weight of polymer in dosage form in grams}}{\text{Molecular Wt of the Polymer}}\right) * (D_p + 3)$$

Wherein, Dp=Degree of Polymerization depending on the grade of polymer, A=degree of substitution of Methoxyl group in the polymer and A=1.4 and 1.9 for Hypromellose 2208 and Hypromellose 2910, respectively. The above values for Dp and A is typical for a given type of hypromellose and can be obtained from the manufacturer's technical sheets/certificates.

By way of example, consider a tablet containing 100 mg of a Hypromellose 2208 of 4000 cP viscosity grade. The total oxyl, methoxyl and hydroxyl contents for the polymer can be calculated as shown below:

From the literature, Hypromellose 2208 has a methoxyl substitution of 1.4, a degree of polymerization of 460 and a molecular wt of 86,000 g/mol. Using these values in the above said equations, the following results are obtained: —

$$\text{Total oxyl content} = \left(\frac{0.1}{86,000}\right) * [3 + \{460*(1.4+1)\}] = 1.29*10^{-03} \text{ moles}$$

$$\text{Total Methoxyl Content} = \left(\frac{0.1}{86,000}\right) * (460*1.4) = 7.49*10^{-04} \text{ moles}$$

$$\text{Total Hydroxyl Content} - \left(\frac{0.1}{86,000}\right) * (460+3) - 5.38*10^{-04} \text{ moles}$$

As used herein, the "total molar oxygen containing groups of the active" is the sum of the oxygen containing groups in the molecule, and can be expressed in terms of moles. It can also be expressed in terms of moles per dosage unit (example, a tablet), which is calculated based on the amount of the oxygen containing groups for that specific active present per dosage unit.

The "total molar oxygen containing groups of the active" in the tablet of the current invention can be calculated by the following equations:

Total molar oxygen containing groups of the active =
$$\left(\frac{\text{Weight of Active in dosage form in grams}}{\text{Molecular Wt of the Active}}\right) * A$$

Wherein A is the number of oxygen containing groups in the "parent" or basic molecular structure. For example, for guaifenesin, A=4; for codeine phosphate, A=3; for hydrocodone bitartrate, A=3. The weight of active in the dosage form is the actual weight of the active used. The molar weight is the weight of one mole of the active expressed in grams. For the purpose of the above calculation, if a salt form is used in the dosage form, the weight of active used and the molar weight should be of the corresponding salt only.

As an example, for a tablet having 30 mg (0.03 g) of Codeine Phosphate, (molecular weight=397.37; number of oxygen-containing groups in the "parent" or basic molecular structure=3) the total molar content of oxygen containing groups can be calculates as Total molar oxygen containing groups in 30 mg Codeine Phosphate =
$$\left(\frac{0.03}{397.37}\right) * 3 = 2.26*10^{-04} \text{ Moles}$$

Similarly, for a tablet having 600 mg (0.6 g) of Guaifenesin (molecular weight=198.22; number of oxygen-containing groups in the "parent" or basic molecular structure=4), the total molar content of oxygen containing groups can be calculated as:

Total molar oxygen containing groups in 600 mg Guaifenesin =
$$\left(\frac{0.6}{198.22}\right) * 4 = 1.21*10^{-02} \text{ Moles}$$

Calculation of ratio of the total molar content of oxyl groups in the hydrophilic polymer to the total molar content of the oxygen containing groups in an active can be calculated as shown below:

$$\left(\frac{\begin{array}{c}\text{Total Oxyl moles for a given}\\ \text{weight of polymer in the dosage form}\end{array}}{\begin{array}{c}\text{Total molar oxygen containing groups}\\ \text{in Active in the dosage form}\end{array}}\right)$$

As used herein, "solid dosage form" of the present invention refers to the unitary dispensable solid dosage comprising a pre-determined amount of the actives in the composition of the invention wherein the dosage form is intended to deliver one therapeutic dose per administration. Examples of known solid dosage forms include without limitation, tablets, capsules, caplets, mini tablets, powders, pellets, granules, triturates, solid solutions etc. In one embodiment the tablet, mini tablet, powder, pellets, and granules may be coated with a suitable a conventional coating material to achieve, for example, greater shelf-life stability (photo-stability, chemical stability, moisture-stability etc), or to enhance identification (color coating) or to enhance the organoleptic perceptions (include flavor and/or sweetener, prevent bad taste and/or odor, etc.). Tablets and caplets may be scored to facilitate division of dosing. The capsules containing powder, pellets or granules or tablets or mini tablets can be also coated. In a specific embodiment, the tablet is a matrix tablet wherein, the two or more actives of the invention can be present as a homogenous admixture within a matrix and presented as a monolithic tablet.

The term "guaifenesin" refers to the expectorant compound (3-(2-methoxyphenoxy)-1,2-propanediol). For the purpose of the current invention, guaifenesin can be used in the form of a 100% pure powder or as a pre-granulate form (for example, for direct compression process) or its equivalent form. It should also be noted that a mixture of the said guaifenesin forms can be used.

The term "codeine" refers to the narcotic as classified under schedule II of DEA controlled substances and refers to the compound itself as well as its pharmaceutically acceptable salts, hydrates, polymorphs, solvates, isomers and the like. Non-limiting examples of pharmaceutically acceptable codeine salts include, but are not limited to, codeine phosphate, codeine hydrochloride, codeine phosphate, codeine sulfate, codeine citrate, and combinations thereof. In one embodiment codeine is in the form of codeine, codeine sulphate, codeine phosphate or combinations thereof. In a specific embodiment, codeine is in the form of codeine sulphate, or codeine phosphate or combinations thereof.

The term "hydrocodone" refers to the narcotic as classified under Schedule II of DEA controlled substances and refers to the compound itself as well as its pharmaceutically acceptable salts, hydrates, polymorphs, solvates, isomers and the like. Non-limiting examples of pharmaceutically acceptable hydrocodone salts include, but are not limited to, hydrocodone bitartrate, and combinations thereof.

The term "substantially free" of a particular component or compound, such as "substantially free of ionic polymer" should be understood as meaning less than 5 wt %, or less than 3 wt % of less than 2 wt % of the total composition. In another aspect, substantially free can refer to less than 1 wt % of the designated component. For example, a composition that is said to be substantially free of ionic polymer can have less than 5 wt %, or less than 3 wt %, or less than 2 wt %, or less than 1 wt % of the ionic polymer. In some embodiments, the compositions and oral dosage forms of the present invention can be free of ionic polymer.

As used herein, the terms "release" and "release rate" are used interchangeably to refer to the discharge or liberation of a substance, including without limitation a drug, from a dosage form into a surrounding environment such as an aqueous medium either in vitro or in vivo.

As used herein, the term "immediate release" refers to the release of active from a dosage form, wherein, $T_{25\%}$ release is less than 0.3 hour, $T_{50\%}$ release is less than 0.5 hour and $T_{75\%}$ release is less than 0.7 hour and wherein the release of dosage form is determined using a USP Type II (paddle) Dissolution Apparatus set at 50 rpm in about 900 mL of 0.1N hydrochloric acid solution in water at about 37° C. The immediate release dosages (for example, in the form of tablet) are used herein to compare with the dosage forms of the current invention. The immediate release dosage form can comprise a single active or a combination of actives that are being compared. In one aspect, the dosage forms of the current invention does not contain any of the actives as an immediate release layer or component or portion, or fraction, nor is a combination of immediate release and sustained release components.

The terms "release rate controlling agent", "release modifying agent", "release modulating agent", and "release modifiers" are used interchangeably and refer to pharmaceutically acceptable agents or devices that are able to alter, delay, target, increase or decrease, or otherwise customize, the release rates of at least one of the contents of the dosage form, when exposed to an aqueous use environment. In one embodiment, the release rate controlling agent is a non-ionic oxyl-containing hydrophilic polymer.

As referred to herein, resistance to "alcohol extraction" or "alcohol associated dose dumping" in presence of alcohol can be tested for the dosage forms of this invention, by subjecting the dosage form to Simulated Gastric Fluid (SGF) with 20% ethanol. A typical manner in order to obtain 900 ml of Simulated Gastric Fluid (SGF) with 20% ethanol/water is by mixing 800 ml of SGF with 210 ml of 95% ethanol/water (which provides 200 ml ethanol) and taking 900 ml of the mixture. Resistance to alcohol extraction can also be tested using an aqueous solution comprising 40% ethanol and performing a drug release testing in presence of alcohol, the results can be compared to the release of drug from the same release medium without alcohol added.

Unless otherwise specified, a drug release rate obtained at a specified time refers to the in vitro drug release rate obtained at the specified time following implementation of an appropriate release testing. The mean time at which a specified percentage of the drug within a dosage form has been released to the medium of test may be referenced as the "$T_{x\%}$" value, where "x" is the percent of drug that has been released. For example, the commonly used reference measurement for evaluating drug release from dosage forms is the time at which 25%, 50% and/or 75% of drug within the dosage form has been released. This measurement is referred to as the "$T_{25\%}$," "$T_{50\%}$," "$T_{75\%}$" for the dosage form.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals. In one embodiment, the subject is a human subject.

The term "oral administration" represents any method of administration in which an active agent can be administered by swallowing, chewing, or sucking of the dosage form. In an embodiment, the pharmaceutical tablet of this invention is swallowed whole with the aid of a liquid such as water, milk, juice and the like.

For the purpose of this invention, unless otherwise stated, administration to a subject under fed condition ("fed treatment") refers to administration such that following an overnight fast of at least 10 hours, the subject starts the test meal 30 minutes prior to administration of the dosage form. The dosage form is administered 30 minutes after start of the test meal, wherein the dosage form is administered with about 240 mL of water. No food is allowed for at least 4 hours post-dose. Water can be allowed as desired except for one hour before and after drug administration.

Similarly, unless specifically mentioned, administration to subjects under fasted condition ("fasted treatment") refers to administration such that following an overnight fast of at least 10 hours, the dosage form is administered with about 240 mL of water to the subject. No food is allowed for at least 4 hours post-dose. Water can be allowed as desired except for one hour before and after drug administration. A "test meal" for evaluating food-effect refers to a high-fat (approximately 50 percent of total caloric content of the meal) and high-calorie (approximately 800 to 1000 calories) meal. The test meal should derive approximately 150, 250, and 500-600 calories from protein, carbohydrate and fat, respectively.

As used herein, "no food effect", "refractory to food intake", "absence of food effect" and the like refer to the property such of an oral dosage form such that following single dose administration of an oral dosage form to a subject under either fed or fasted conditions, the variation in the pharmacokinetic parameters for the active agents in the oral dosage form is not more than about 40% as compared to the same pharmacokinetic parameter measured in the same subject when the oral dosage form is administered under the opposite condition (i.e. fed vs. fasted). In one embodiment, the pharmacokinetic parameters, particularly the plasma mean $C_{max}$ or the mean $AUC_{0-inf}$ or both, for the respective actives does not vary by more than about 30% when administered under a fed versus a fasted condition.

As used herein, "steady state" or "$C_{ss}$" refers to the concentration of an active in a body fluid (usually plasma) when the rates of drug administration and drug elimination are equal. $C_{ss}$ is a value approached as a limit and is achieved, theoretically, following the last of an infinite number of equal doses given at equal intervals. $C_{ss}$ max) is the maximum value under steady state conditions and $C_{ss}$ min is the minimum value achieved under steady state conditions.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

With this in mind, the present invention provides for pharmaceutical tablets for delivering at least two actives, at least one of which is a tri-oxy active agent. In one embodiment, a pharmaceutical tablet for oral administration once every 12 hours is provided. The tablet includes a first active agent that is a tri-oxy active agent, a second active agent, and a release rate controlling non-ionic oxyl-containing hydrophilic polymer. The total oxyl content of the hydrophilic polymer in the tablet is from about $4 \times 10^{-4}$ moles to about $2.0 \times 10^{-3}$ moles. The tablet is a matrix tablet and a single-dose administration of one or more tablets to a subject under fasted conditions provides a mean $C_{max}$ for each of the first active agent and the second active agent that is 70% to 135% of a respective mean $C_{max}$ provided by administering an immediate release oral dosage to a subject under fasted conditions every 4 to 6 hours over a 12 hour time period, wherein cumulative dosage amounts administered over the 12 hour time period of each active agent in the immediate release oral dosage is equivalent to the respective amount of each active agent in the pharmaceutical tablet.

In another embodiment, a pharmaceutical tablet for oral administration once every 12 hours is provided. The tablet includes a first active agent that is a tri-oxy active agent, a second active agent, and a release rate controlling non-ionic oxyl-containing hydrophilic polymer. The total oxyl content of the hydrophilic polymer in the tablet is from about $4 \times 10^{-4}$ moles to about $2.0 \times 10^{-3}$ moles. The tablet is a matrix tablet and a single-dose administration of one or more tablets to a subject under fed conditions provides a mean $C_{max}$ for each of the first active agent and the second active agent that is 70% to 135% of a respective mean $C_{max}$ provided by administering an immediate release oral dosage to a subject under fed conditions every 4 to 6 hours over a 12 hour time period, wherein cumulative dosage amounts administered over the 12 hour time period of each active agent in the immediate release oral dosage is equivalent to the respective amount of each active agent in the pharmaceutical tablet.

In another embodiment, a pharmaceutical tablet for oral administration once every 12 hours is provided. The tablet includes a first active agent that is a tri-oxy active agent, a second active agent, and a release rate controlling non-ionic oxyl-containing hydrophilic polymer. The total oxyl content of the hydrophilic polymer in the tablet is from about $4 \times 10^{-4}$ moles to about $2.0 \times 10^{-3}$ moles. The tablet is a matrix tablet and a single-dose administration of one or more tablets to a subject under fasted conditions every twelve hours provides a mean $C_{max}$ for each of the first active agent and the second active agent that is 70% to 135% of a respective mean $C_{max}$ provided by administering the same oral dosage to the subject under fed conditions every 12 hours. The same amount of each active agent is administered over any given 12 hour period.

In another embodiment, a pharmaceutical tablet for dosing once every 12 hours is provided. The tablet is a matrix tablet and includes a first active agent that is a tri-oxy active agent, a second active agent, and a release rate controlling non-ionic oxyl-containing hydrophilic polymer. The tablet is formulated such that when placed in a USP Type 2 dissolution apparatus at 50 rpm in 900 mL of 0.1 N hydrochloric acid solution in water at 37° C., about 50 wt % of the first active agent is released in about 1.5 hours to about 3.8 hours. The ratio of the amount of first active released from the tablet to the amount of second active agent released at 1 hour and at 4 hours is between about 0.7:1 and about 1.3:1. In one embodiment, the tablets of the present invention can be single layer tablets. In other words, the active agents are present in a common tablet matrix and not separated into distinct active agent layers.

In yet a further embodiment, the present invention provides for a method of treating cough and/or cold symptoms in a human subject, comprising administering to the human subject a pharmaceutical tablet in accordance with one of the embodiments of the present invention. In yet another embodiment, a method of minimizing sleep disturbance for a human subject having cough and/or cold symptoms is provided in which the method comprises administering to the human subject a pharmaceutical tablet in accordance with an embodiment of the present invention. In one aspect, the methods of the present invention can be accomplished without regard to food consumption. In one embodiment, the mean $C_{max}$ of the first active agent will vary not more than 40% when administered with food as compared to administration of the same tablet to the same subject without food.

The oral dosage forms disclosed herein can be, but do not have to be, administered with food (or meals). In one embodiment, the composition or oral dosage capsule can be administered with a meal, such as a meal that provides about 200 to about 1000 calories of energy. In another embodiment, the oral dosage form can be administered with a standard meal. In another embodiment, the oral dosage form can be administered with a meal has no fat, low fat, medium fat or high fat. The compositional make-up of the meals that are administered can vary depending on the tastes and dietary needs of a subject.

The oral dosage forms (e.g. tablets) disclosed herein can be orally administered in a 12 hours' dosing regimen or as "12 hour dosing" that is suitable to the needs of the subject. The dosage form is also referred to as or "12 hour dosage form", or "12 hour product". The 12 hours' dosing regimen can include administering the dosage forms in the morning, in the evening, at about night time or combinations thereof. The 12 hours' dosing regimen can include dosing one or more dosage units at one or more administration times. In one embodiment, the pharmaceutical dosage forms of the current invention can be administered once every 12 hours. Further, the pharmaceutical dosage forms of the current invention can be administered twice in a day (or about 24 hours) usually about 12 hours apart. In another embodiment, the pharmaceutical dosage form of the current invention is administered once every 12 hours as a single oral dosage tablet.

In one embodiment, the 12 hour oral dosage forms of the invention has no food-effect wherein, the dosage form provides upon a single dose administration to a subject under fed and fasted conditions, a ratios of the corresponding mean $C_{max}$ or $AUC_{0-inf}$, or both, for the respective actives between fed and fasted treatments, in the range between about 0.7 and about 1.3. In another specific embodiment, the 12 hour oral dosage forms of the invention provides upon a single dose administration to a subject under fed and fasted conditions, a ratio of the mean $AUC_{0-inf}$ or $AUC_{0-t}$ or both, for the respective active between fed and fasted treatments, in the range between 0.7 and 1.3.

The pharmaceutical tablets of the present invention include a first active agent, which is a tri-oxy active agent. In one embodiment, the first active agent can be codeine or its pharmaceutically acceptable salts. In another embodiment, the first active agent can be guaifenesin. It yet another embodiment, the first active agent can be hydrocodone or its pharmaceutically acceptable salts.

The pharmaceutical tablets of the present invention include a second active agent, wherein, the second active agent can, but does not need to, be a tri-oxy active. Thus, in some embodiments the tablet can include a first and a second active agent that that are each tri-oxy active agents, while in other embodiments the second active agent can be a non-tri-oxy active agent. Non-limiting examples of non-tri-oxy second active agents that can be used in the tablets can include chlorpheniramine, cyclopentamine, dexchlorpheniramine, diphenhydramine, brompheniramine, dexbrompheniramine, dextromethorphan tripolidine, desloratadine, cyproheptadine, phenylephrine, pyrallamine, pseudoephedrine, azalastin, loratidine, theophylline, their salts or esters thereof, and combinations thereof. In one embodiment, the second active agent is a non-tri-oxy active agent. In another embodiment, the second active agent is chlorpheniramine or its pharmaceutically acceptable salt. Exemplary embodiments of first and second active agent combinations include, but are not limited to, codeine and guaifenesin, codeine and chlorpheniramine, guaifenesin and hydrocodone, guaifenesin and chlorpheniramine, and hydrocodone and chlorpheniramine, codeine and pseudoephedrine, guaifenesin and pseudoephedrine, guaifenesin and dextromethorphan, codeine and dextromethorphan, hydrocodone and chlorpheniramine; hydrocodone, chlorpheniramine and pseudoephedrine or phenylephrine.

The pharmaceutical tablets of the present invention also include a non-ionic oxyl-containing hydrophilic polymer. In one embodiment, the non-ionic hydrophilic polymer is a release-rate controlling polymer. In some embodiments, the tablets are also free, or substantially free, of ionic polymers. Non-limiting examples of non-ionic release-rate controlling hydrophilic polymers that can be used include cellulose polymers such as hydroxypropyl cellulose, methyl cellulose, carboxymethyl cellulose, hydroxypropyl methyl cellulose, combinations thereof, and the like.

In one embodiment, the hydrophilic polymer is a cellulose polymer. In another embodiment, the hydrophilic polymer is a hydroxypropyl methyl cellulose. In a specific embodiment, the polymer has an average methoxy content of about 15 mole % to about 30 mole %. In another specific embodiment, the polymer has an average methoxy content of about 18 mole % to about 25 mole %. In another embodiment, when used in a tablet dosage form of the invention, the total oxyl content of the hydrophilic polymer in the tablet is from about $4 \times 10^{-4}$ moles to about $2.0 \times 10^{-3}$ moles. In further embodiment, when used in a tablet dosage form of the invention, the hydrophilic polymer provides a methoxy content of about $2.2 \times 10^{-4}$ to $1.2 \times 10^{-3}$ moles per tablet. It should be noted that a mixture of the said hydroxypropyl methyl celluloses can be used wherein the requisite range of methoxyl content per dosage form (example, tablet) is obtained.

In still further embodiments, when the cellulose polymer is hydroxypropyl methyl cellulose, it can be present in the tablet in an amount of about 40 mg to about 175 mg, or in an amount of about 60 mg to about 150 mg, or in an amount of about 60 mg to about 125 mg. In a specific embodiment, the hydroxypropyl methyl cellulose can have an average apparent viscosity of about 3000 cP to about 15000 cP when determined on a 2% solution in water at 20° C. In another embodiment, the hydroxypropyl methyl cellulose can have an average apparent viscosity of about 3000 cP to about 5000 cP when determined on a 2% solution in water at 20° C. It should be noted that a mixture of hydroxypropyl methyl celluloses can be used to achieve a desired viscosity within the above defined ranges.

Without being limited by theory, it is believed that there exists an interaction at the molecular level between the oxyl-content of the non-ionic hydrophilic cellulose polymer and the oxygen-containing groups in the tri-oxy actives of the invention. It is believed that this interaction influences the rate and extent of hydration, gelation and/or erosion of the polymer which in turn enables the requisite performance for a matrix tablet formulated for administration once every twelve hours. Therefore, a particular range of the amount of the non-ionic polymer in a tri-oxy active combination solid dosage form (e.g. matrix tablet) can provide a release profile which enables 12 hour dosing. Accordingly, Applicants have discovered that a total oxyl content of $4 \times 10^{-4}$ moles to about $2.0 \times 10^{-3}$ moles from the polymer per dosage form (e.g. tablet) enables a 12 hour dosing therapy of at least one tri-oxy active in combination with another active of the invention. Applicants further believe that one or more of the oxygen containing groups in the tri-oxy active is responsible for the synergistic effect with the oxyl-containing polymer. Furthermore, the levels of the oxyl-containing polymer enabling a 12 hour solid dosage form is specific to an active that contains at least three oxygen-containing groups; preferably at least one of each of methoxyl group and ether groups and at least one of carbonyl or hydroxyl groups. In contrast, as seen through some of the experimental examples disclosed herein, a higher or lower methoxy content of the polymer can result in an undesirably fast or very slow release of the actives from the dosage form thereby failing to comply with the typical requirements for the 12 hour dosing regimen.

The pharmaceutical tablets of the present invention can be formulated such that upon single-dose administration of one or more tablets to a subject under fasted conditions, the tablets can provide a mean $AUC_{inf}$ of each of the first active agent and the second active agent that is 70% to 135% of a respective mean $AUC_{inf}$ provided by administering an immediate release oral dosage to a subject under fasted conditions every 4 to 6 hours over a 12 hour time period. The cumulative dosage amounts administered over the 12 hour time period of each active agent in the immediate release oral dosage is equivalent to the respective amount of each active agent in the pharmaceutical tablet. Similarly, the tablets can be formulated such that upon single-dose administration of one or more tablets to a subject under fasted conditions provides a mean $AUC_{0-12}$ of each of the first active agent and the second active agent that is 70% to 135% of a respective mean $AUC_{0-12}$ provided by administering an immediate release oral dosage to a subject under fasted conditions every 4 to 6 hours over a 12 hour time period. As above, the cumulative dosage amounts administered over the 12 hour time period of each active agent in the immediate release oral dosage is equivalent to the respective amount of each active agent in the pharmaceutical tablet.

In one embodiment, the first active agent is codeine or its pharmaceutically acceptable salt. In one embodiment, the codeine can be resin free or substantially resin free. The codeine can comprise about 35 wt % or less, of the total tablet weight. The codeine can comprise from about 20 wt % to about 35 wt % of the total tablet weight. In another embodiment, the codeine can comprise about 25 wt % to about 30 wt % of the total tablet weight. In another embodiment, the codeine can comprise about 3 wt % to about 5 wt % of the total tablet weight. In a further embodiment, the codeine can comprise about 3.5 wt % to about 4 wt % of the total tablet weight. In another embodiment, when the first active agent is codeine, the ratio of total content of the oxyl groups in the hydrophilic polymer to the total molar content of the oxygen-containing groups in the codeine is from about 2.5 to about 9. In another embodiment, when the first active agent is codeine, the ratio of total content of the oxyl groups in the hydrophilic polymer to the total molar content of the oxygen-containing groups in the codeine is from about 2.5 to about 4.5.

In a further embodiment, the tablet can have a first active agent of codeine or its pharmaceutically acceptable salts and the second active agent can be chlorpheniramine or a pharmaceutically acceptable salt thereof. The codeine and chlorpheniramine tablet can, upon single-dose administration to a subject under fasted conditions, provide a mean $T_{max}$ for codeine of about 2.2 hours to about 3.4 hours and a mean $T_{max}$ for chlorpheniramine of about 5 hours about 14 hours. In another aspect, the codeine and chlorpheniramine tablet can, when placed in a USP Type 2 dissolution apparatus at 50 rpm in 900 mL of 0.1 N hydrochloric acid solution in water at 37° C., provide a release of the active agents such that about 30% to about 40% of the amount of codeine is released in the first 0.5 to 1 hour, and the amount of chlorpheniramine released in the same time is between 80% and 120% of the amount of codeine released. In another aspect, when placed in a USP Type 2 dissolution apparatus at 50 rpm in 900 mL of 0.1 N hydrochloric acid solution in water at 37° C., the time to release about 50 wt % of the codeine and chlorpheniramine is about 1.5 to about 3 hrs. In another aspect, when placed in a USP Type 2 dissolution apparatus at 50 rpm in 900 mL of 0.1 N hydrochloric acid solution in water at 37° C., the time to release about 50 wt % of the codeine and chlorpheniramine is about 1.6 to about 2.4 hrs. In yet a further embodiment, the tablet can provide a release of about 45-60% of the amount of codeine and about 45-60% of the amount of chlorpheniramine in about 2 hours. In yet a further aspect, when placed in a USP Type 2 dissolution apparatus at 50 rpm in 900 mL of 0.1 N hydrochloric acid solution in water at 37° C., the tablet can provide a release of the active agents such that at least about 70% of the amount of chlorpheniramine is released in about 3 hours to 4 hours, and the amount of codeine released in the same time period is between 80% and 120% of the amount of chlorpheniramine released. In still a further embodiment, the pharmaceutical tablet can be formulated such that when placed in a USP Type 2 dissolution apparatus at 50 rpm in 900 mL of 0.1 N hydrochloric acid solution in water at 37° C., the ratio of the amount of first active released to the amount of second active agent released at a single time point between 1 hour and 4 hours is about 0.8:1 and about 1.2:1.

In one embodiment, the dosage forms of the current invention can include a third active agent. The third active agent can be a tri-oxy active agent or a non-tri-oxy active agent. In one embodiment, the active agent can be a decongestant. In one embodiment, the decongestant can be pseudoephedrine, phenylephrine, and their pharmaceutically acceptable salts. Example combinations of first, second, and third active agents that can be combined in the pharmaceutical tablets of the present invention include, without limitation, 1) codeine, chlorpheniramine, and pseudoephedrine; 2) codeine, chlorpheniramine, and phenylephrine; 3) codeine, guaifenesin, and pseudoephedrine; 4) codeine, guaifenesin, and phenylephrine; 5) guaifenesin, hydrocodone, and pseudoephedrine; 6) guaifenesin, hydrocodone, and phenylephrine; and the like.

In one aspect, a single-dose administration of one or more tablets to a subject under fasted conditions can provide a mean $C_{max}$ for each of the first active agent, second active agent and the third active agent that is about 70% to about 135% of a respective mean $C_{max}$ provided by administering an immediate release oral dosage, as a combination or respective single active dosage form, to a subject under fasted conditions every 4 to 6 hours over a 12 hour time period, wherein cumulative dosage amounts administered over the 12 hour time period of each active agent from the immediate release dosage forms are equivalent to the respective amount of each active agent in the pharmaceutical tablet. In one aspect, the pharmaceutical matrix tablet of the current invention, with the three actives, when placed in a USP Type 2 dissolution apparatus at 50 rpm in 900 mL of 0.1 N hydrochloric acid solution in water at 37° C., where in the amount of second and third active released is within 70% to 135% of release of first active when measured between about 1 and 4 hours.

In a further embodiment, the first active agent is codeine and the second active agent is guaifenesin. It is noteworthy that because both the codeine and the guaifenesin are tri-oxy active agents and either of them could be considered as the first active agent. The codeine can be present in the amounts discussed above, and the guaifenesin can be present in amounts of about 600 mg/tablet to about 1200 mg/tablet. In another embodiment, the guaifenesin can be present in an amount of 600 mg/tablet. In one embodiment, the codeine can be present in an amount of about 30 mg, the guaifenesin can be present in an amount of about 600 mg, and the hydrophilic polymer can be hydroxypropyl methyl cellulose and comprises about 8 wt % to about 20 wt % of the tablet. In a still further specific embodiment, the hydrophilic polymer can be hydroxypropyl methyl cellulose and comprises about 8 wt % to about 15 wt % of the tablet.

In another embodiment, the pharmaceutical tablet includes codeine and guaifenesin and upon administration to a subject under fasted conditions the tablet provides a guaifenesin $C_{min}$ of about 3 ng/mL or more, at steady state. In another embodiment, the tablet provides at steady state, a guaifenesin mean $C_{max}$ of about 850 ng/mL to about 1700 ng/mL, and a codeine mean $C_{max}$ of about 30 ng/mL to about 90 ng/mL.

In one aspect, when placed in a USP Type 2 dissolution apparatus at 50 rpm in 900 mL of 0.1 N hydrochloric acid solution in water at 37° C., the $T_{25\%}$ for both codeine and the guaifenesin is about 0.5-1 hour and the $T_{75\%}$ for both the codeine and the guaifenesin is about 5 hours. In another aspect, when the tablet is placed in a USP Type 2 dissolution apparatus at 50 rpm in 900 mL of 0.1 N hydrochloric acid solution in water at 37° C., about 25% to about 35% of the amount of guaifenesin is released in the 0.5-1 hour, and the amount of codeine released in the same time is between 70% and 130% of the amount of guaifenesin released. In another aspect, when the tablet is placed in a USP Type 2 dissolution apparatus at 50 rpm in 900 mL of 0.1 N hydrochloric acid solution in water at 37° C., about 50 wt % of each of the guaifenesin and the codeine are released in about 1.5 to about 3 hours. In another embodiment, when the tablet is placed in a USP Type 2 dissolution apparatus at 50 rpm in 900 mL of 0.1 N hydrochloric acid solution in water at 37° C., about 50 wt % of each of the guaifenesin and the codeine are released in about 1.6-2.4 hours. In still a further aspect, when the tablet is placed in a USP Type 2 dissolution apparatus at 50 rpm in 900 mL of 0.1 N hydrochloric acid solution in water at 37° C., at least about 80% of the amount of codeine is released in about 8 hours, and the amount of guaifenesin released in the same time period is between 80% and 120% of the amount of codeine released. In one embodiment, the when the active agents are codeine and guaifenesin and the dissolution is accomplished according to the methodologies described above, the ratio of the amount of first active released to the amount of second active agent released at a single time point between 1.5 hours and 4 hours is about. 0.7:1 and about 1.3:1.

In a further embodiment, the first active agent can be guaifenesin. The guaifenesin can be present in amounts of about 600 mg/tablet to about 1200 mg/tablet. In one embodiment, the guaifenesin can be present in an amount of 600 mg/tablet. In one embodiment, the ratio of the total molar content of oxyl groups in the hydrophilic polymer to the total molar content of the oxygen containing groups in the guaifenesin can be about 0.07 to 0.18. When guaifenesin is the first active agent, the second active agent can be hydrocodone. Like guaifenesin, hydrocodone is a tri-oxy active agent and thus either of them could be considered to be the first active agent in a tablet having both guaifenesin and hydrocodone. In the guaifenesin-hydrocodone combination tablet, in one embodiment the tablet can be such that upon administration to a subject the tablet can provide a guaifenesin $C_{min}$ of about 3 ng/mL or more, at steady state. In one embodiment, the tablet can be such that the guaifenesin can be present in an amount of about 600 mg to about 1200 mg, the hydrocodone can be present in an amount of 5 mg to 10 mg, and the hydrophilic polymer can be hydroxypropyl methyl cellulose and can be present in an amount of 55 mg to about 165 mg.

In still a further embodiment, the tablet can be such that the guaifenesin can be present in an amount of about 600 mg/tablet, the hydrocodone can be present in an amount of 5 mg/tablet, and the hydrophilic polymer can be hydroxypropyl methyl cellulose and comprises about 8 wt % to about 20 wt % of the tablet. In another specific embodiment, the hydrophilic polymer can be hydroxypropyl methyl cellulose and comprises about 8 wt % to about 15 wt % of the tablet. In another embodiment, the tablet provides at steady state, a guaifenesin mean $C_{max}$ of about 850 ng/mL to 1700 ng/mL, and a hydrocodone mean $C_{max}$ of about 12 ng/mL to 25 ng/mL.

When the pharmaceutical tablets include guaifenesin and hydrocodone as the first and second active agents respectively, the tablet can be formulated such that when placed in a USP Type 2 dissolution apparatus at 50 rpm in 900 mL of 0.1 N hydrochloric acid solution in water at 37° C., the $T_{25\%}$ for both guaifenesin and the hydrocodone is from about 25 minutes to about 75 minutes and the $T_{75\%}$ for both the guaifenesin and the hydrocodone is from about 3 hours to about 7 hours. In another embodiment, the tablet can be formulated such that when placed in a USP Type 2 dissolution apparatus at 50 rpm in 900 mL of 0.1 N hydrochloric acid solution in water at 37° C., about 35% or less of the amount of guaifenesin and about 20% to 40% of the amount of the hydrocodone are released in 0.5-1 hour. In yet a further embodiment, the tablet can be formulated such that when placed in a USP Type 2 dissolution apparatus at 50 rpm in 900 mL of 0.1 N hydrochloric acid solution in water at 37° C., about 40-65% of the amount of guaifenesin and about 40-65% of the amount of hydrocodone are released in about 2 hours. In another embodiment, the tablet can be formulated such that wherein when placed in a USP Type 2 dissolution apparatus at 50 rpm in 900 mL of 0.1 N hydrochloric acid solution in water at 37° C., the time to release about 50% of the amount of guaifenesin and of hydrocodone is about 2 hours.

In another embodiment, the tablet can be formulated such that when placed in a USP Type 2 dissolution apparatus at 50 rpm in 900 mL of 0.1 N hydrochloric acid solution in water at 37° C., about 35% or less of the amount of guaifenesin and about 20-40% the amount of guaifenesin is released in the first 0.5-1 hour, and the amount of hydrocodone released in the same time is between 70% and 130% of the amount of guaifenesin released.

In still a further embodiment the tablet can be formulated such that when placed in a USP Type 2 dissolution apparatus at 50 rpm in 900 mL of 0.1 N hydrochloric acid solution in water at 37° C., at least about 80% of the amount of hydrocodone is released in about 8 hours, and the amount of guaifenesin released in the same time period is between 80% and 120% of the amount of hydrocodone released. In yet another embodiment, when the active agents are guaifenesin and hydrocodone and the release of the actives is determined according to the methodologies described above, the ratio of the amount of first active released to the amount of second active agent released at a single time point between 1.5 hours and 4 hours is about 0.7:1 and about 1.3:1.

In still a further embodiment the tablet can be formulated such that when placed in a USP Type 2 dissolution apparatus at 50 rpm in 900 mL of 0.1 N hydrochloric acid solution in water at 37° C., at least about 80% of the amount of hydrocodone is released in about 8 hours, and the amount of guaifenesin released in the same time period is between 80% and 120% of the amount of guaifenesin released.

In some embodiments, the first active agent can be hydrocodone or its pharmaceutically active salts. The hydrocodone can comprise 0.5 wt % to about 1 wt % of the tablets and can be present in amounts of about 5 mg/tablet to about 10 mg/tablet. In embodiments where hydrocodone is the first active agent the non-ionic hydrophilic polymer can be hydroxypropyl methyl cellulose and can be present in amounts of 40 mg/tablet to about 175 mg/tablet.

In another aspect, the matrix tablet of the current invention can be formulated such that it does not exhibit "dose dumping" effect when tested in vitro in a USP Type 2 dissolution apparatus at 50 rpm in 900 mL of 0.1 N hydrochloric acid solution in water containing from about 4%-40% v/v of ethanol, at 37° C. Accordingly, in one embodiment, the tablet does not release the entire amount of the tri-oxy active in about 2 hours or less. In another embodiment, the amount of the tri-oxy active released from the tablet under the said in vitro "dose dumping" release testing conditions is about 180% or less, preferably, about 150% or less or even more preferably 130% or less of the amount of the respective tri-oxy active released in about 2 hours in a 900 mL 0.1 N hydrochloric acid solution in water but without ethanol, at 37° C., taken in a USP Type 2 dissolution apparatus at 50 rpm.

The compositions and the solid oral dosage forms (example, tablets) of the current invention can also include one or more of the pharmaceutical process aids selected from the group known in the art, consisting of binders, bufferants, compacting aids, diluents, disintegrants, flavors, colorants, taste-masking agents, pH modifiers, lubricants, glidants, thickening agent, opacifying agent, humectants, desiccants, effervescing agents, sweeteners, plasticizing agents, wetting agents and the like. The amount of each of these excipients per dosage form (example, matrix tablet) can vary depending on the amount of the actives and non-ionic oxyl-containing hydrophilic polymer in the dosage form. For example, the tabletting aids are added in amounts typically known to one of relevant skill in the art. Non-limiting examples of the tabletting aids suitable for use in the pharmaceutical tablets of the present invention include non-crystalline cellulose; microcrystalline cellulose; dextrose; croscarmellose; cyclodextrins; β-cyclodextrins; α-cyclodextrin; dextrates; sorbitol; lactose; sucrose; maltose; galactose; polyvinylpyrrolidone (povidone K 12 to K120); crospovidone; polyvinyl alcohol; glycerol; glucose; polyols such as mannitol; xylitol or sorbitol or their combinations; polyethylene glycol esters; alginates; sodium alginate; poly(lactide coglycolide); gelatin; crosslinked gelatin; agar-agar; sodium dodecyl sulfate; glycerin; polyethylene glycols of mol wt range from about 100 to about 20,000 or their mixtures; lactose; guar gum; xanthan gum; starches; gum arabic; dextrins; dibasic calcium phosphate; cyclodextrins or its derivatives and their combinations; sodium starch glycolate; croscarmellose sodium; galactomannan; tricalcium phosphate; maltodextrin or its derivatives and their combinations; polyoxyethylene stearate; carnuaba wax; fatty alcohols; sugar esters; sugar ethers; shellacs; tocopherol; tocopherol polyethyleneglycol succinate; tocopherol succinate; tocopherol acetate; talc, magnesium stearate, stearic acid, sodium lauryl sulphate, and the like.

The solid oral dosage forms from the present invention can be manufactured as tablet or capsule dosage forms either by dry blending/granulation methods, or by wet granulation methods. For example, the actives can be combined with one or more pharmaceutically acceptable excipients/aids described above and blended to get a homogenous mixture which can be compressed into a tablet or into mini tablets to be disposed into a capsule. In another embodiment, the homogenous mixture can be kneaded with a binder solution to get a wet granulate mass which can be dried and sized, for example by passing through ASTM mesh #30. The resulting granules can be optionally blended with pharmaceutical aids such as diluents, lubricants, disintegrants etc, and disposed into capsules or compressed into tablets. In another particular case, the tablets can be coated. Non-limiting examples of the processes that can be used to prepare the compositions and dosage forms of this invention include mixing melting, prilling, size reduction, melt-spray congealing, co-precipitation, co-crystallization, encapsulation, co-milling, spry or freeze drying, complexing, granulating, extruding, slugging, or combinations thereof.

The solid oral dosage forms can also be formulated using melt-extrusion processes alone or in combination with other known processes. For example, in one embodiment, the required amounts of the actives and non-ionic oxyl-containing hydrophilic polymer can be homogeneously combined with a sufficient amount of one or more pharmaceutical excipients/tableting aids prior to undergoing extrusion.

The dosage forms of the invention provide "no food effect" or the dosage form is "refractory to food intake". Accordingly, in one embodiment, the pharmacokinetic parameters, particularly the plasma mean $C_{max}$, and the mean $AUC_{0-inf}$ for the respective actives following a single dose administration of the dosage form under fed or fasted conditions, does not vary by more than about 40%. In a preferred embodiment, the pharmacokinetic parameters, particularly the plasma mean $C_{max}$, and the mean $AUC_{0-inf}$ for the respective actives does not vary by more than about 30%. In another embodiment, the dosage forms of the invention has no food-effect and the dosage form provides, upon a single dose administration to a subject under fed and fasted conditions, a ratio of the corresponding mean $C_{max}$, or $AUC_{0-inf}$, or both, for the respective actives between fed and fasted treatments, in the range between about 0.7 and about 1.3. In still another embodiment, the dosage form of the current invention provides, upon a single dose administration to a subject under fed and fasted conditions, a ratio of the mean $AUC_{0-inf}$ or $AUC_{0-t}$, or both, for the respective active between fed and fasted treatments, in the range between 0.7 and 1.3.

In another aspect, the present invention discloses pharmaceutical solid dosage form such as matrix tablet wherein, for a given dose levels of two actives, at least one of which is a tri-oxy active, an optimal non-ionic oxyl-containing hydrophilic polymer level is tied to an optimal Pk of each of both the actives, that is robust to differential dose levels of the actives for 12 hour dosing.

EXAMPLES

The following examples are provided to promote a more clear understanding of certain embodiments of the present invention, and are in no way meant as a limitation thereon. Unless otherwise specified or mentioned, all the compositions provided in the examples are by measure of weight in the final composition.

Example 1

In Vitro Release Profiles of the Actives from Dosage Forms

The in vitro release profiles of the respective actives from the dosage form examples of the current invention were determined using a USP Type II (paddle) Dissolution Apparatus set at 50 rpm in about 900 mL of 0.1N hydrochloric acid solution in water at about 37° C. Aliquots sampled from the dissolution apparatus at pre-determined time intervals varying from about 5 minutes up to about 36 hours were analyzed for the respective actives by employing an HPLC with a UV spectrophotometer detector and using appropriate standard solutions. The amount of the active released is then calculated from the concentrations of actives in the medium and the volume of the medium, and expressed as a percentage of their amounts originally present in the dosage form.

Example 2

In Vivo Pharmacokinetic Evaluation of the Dosage Forms

Dosage forms of examples where indicated, were evaluated for in vivo pharmacokinetic performance. The general study design was an open-label, randomized, single-dose, crossover performed on 10-12 volunteers. In each treatment period, subjects were housed from at least 12 hours before dosing until after the 24-hour blood draw. There was at least 5-day washout between treatment periods, during the study. The analysis of the plasma samples were carried out for the respective drugs using LC-MS/MS.

The $C_{max}$, $T_{max}$, $AUC_{0-t}$ and $AUC_{0-\infty}$ were calculated for the first and second actives in the plasma of the test subjects. Pharmacokinetic and statistical analyses were performed on the data obtained from the subjects using Pharsight® WinNonlin®. The pharmacokinetic parameters are defined as follows:

$AUC_{0-t}$: The area under the plasma concentration vs. time curve, from zero time to last measurable concentration of the drug, as calculated by the linear trapezoidal method.

AUC ($AUC_{0-\infty}$): The area under the plasma concentration versus time curve from time 0 to infinity. AUC was calculated as the sum of the AUC0-t plus the ratio of the last measurable plasma concentration of the administered drug to the elimination rate constant.

$C_{max}$: The maximum measured plasma concentration of the administered drug.

$C_{12}$: The plasma concentration of the administered drug 12 hours post-dosing.

$T_{max}$: The time at which the maximum measured plasma concentration of the administered drug is achieved $C_{min}$: Minimum concentration of an active in the plasma measured during steady state. It can be the minimum concentration observed during the dosing period, in a single-dose study.

Mean: Average value of measured parameter of all individual subjects.

Example 3-15

Dosage Forms Having at Least One Tri-Oxy Active and at Least One Oxyl-Containing Non-Ionic Hydrophilic Polymer Tablet dosage forms having the compositions as recited in Examples 3 through 15 are prepared by using the respective components shown in Tables I and II.

TABLE I

| INGREDIENT * | EXAMPLE | | | | | | | |
|---|---|---|---|---|---|---|---|---|
| | 3 | 4 | 5 | 6 | 7 | 8 | 9 | 10 |
| First Active (Tri-oxy active), mg [e.g. Codeine Phosphate, CP] | 54 | 54 | 54 | 54 | 54 | 54 | 54 | 54 |
| Second Active (Non-oxo active), mg [e.g. Chlorpheniramine Maleate, CPM] | 8 | 8 | 8 | 8 | 8 | 8 | 8 | 8 |
| Oxyl-containing non-ionic hydrophilic polymer, mg [e.g. Hypromellose 2208] | 25 | 75 | 200 | 450 | 65 | 85 | — | 50 |
| Oxyl-containing non-ionic hydrophilic polymer, mg [e.g. Hypromellose 2910] | — | — | — | — | — | — | 57 | 19 |
| Pharmaceutical Processing Aids, mg | 65 | 65 | 105 | 160 | 75 | 65 | 73 | 80 |
| Total Methoxyl Content of the non-ionic hydrophilic polymer, (mMol.) | 0.19 | 0.56 | 1.50 | 3.37 | 0.49 | 0.64 | 0.58 | 0.57 |
| Total Hydroxyl Content of the non-ionic hydrophilic polymer (mMol.) | 0.13 | 0.40 | 1.08 | 2.42 | 0.35 | 0.46 | 0.31 | 0.37 |
| Total Oxyl Content of the non-ionic hydrophilic polymer (mMol.) | 0.32 | 0.97 | 2.57 | 5.79 | 0.84 | 1.09 | 0.89 | 0.94 |
| Total Molar Content of the Oxygen Containing Groups in Codeine (mMol.) | 0.41 | 0.41 | 0.41 | 0.41 | 0.41 | 0.41 | 0.41 | 0.41 |
| Ratio of the total molar content of oxyl groups in the hydrophilic polymer to the total molar content of the oxygen containing groups in Codeine Phosphate | 0.78 | 2.38 | 6.30 | 14.2 | 2.06 | 2.67 | 2.17 | 2.30 |

* Excipients shown are exemplary of the classes; additional Pharmaceutical Processing aids known in the art can be used.

TABLE II

| INGREDIENT * | EXAMPLE | | | | |
|---|---|---|---|---|---|
| | 11 mg | 12 mg | 13 mg | 14 mg | 15 mg |
| First Active (Tri-oxy active) [e.g. Codeine Phosphate, CP] | 27 | 54 | 54 | 54 | 40 |
| Second Active (Non-oxo active) [e.g. Chlorpheniramine Maleate, CPM] | 4 | 8 | 8 | — | — |
| Second Active (Non-oxo active) [e.g. Pseudoephedrine, SUD] | — | — | — | — | 120 |

TABLE II-continued

| INGREDIENT * | EXAMPLE | | | | |
|---|---|---|---|---|---|
| | 11 mg | 12 mg | 13 mg | 14 mg | 15 mg |
| Second Active (Non-oxo active) [e.g. Phenylephrine, PE] | — | — | — | 30-60 | — |
| Third Active [e.g. Pseudoephedrine, SUD] | — | 120 | — | — | — |
| Third Active [e.g. Phenylephrine, PE] | — | — | 30-60 | — | — |
| Oxyl-containing non-ionic hydrophilic polymer [e.g. Hypromellose 2208] | — | 70-135 | 70-135 | 70-135 | 70-135 |
| Pharmaceutical Processing Aids | 155 | 55-80 | 55-80 | 55-80 | 55-80 |

* Excipients shown are exemplary of the classes; additional Pharmaceutical Processing aids known in the art can be used.

Procedure for Preparing the Tablets of Examples 1 to 15 is as Follows:

The actives are separately sifted through a clean ASTM Mesh No. 60 and thoroughly mixed by serial addition method. The actives are mixed thoroughly and the non-ionic hydrophilic polymer(s) are passed through the ASTM Mesh No. 60 and blended with the mixture of the actives. The powder admixture is blended with the previously sieved (ASTM mesh No. 60) and collected pharmaceutical aids (diluents, lubricants etc) The resulting powder blend is then compressed into tablets using 8 or 10 mm diameter round die-punch tooling fitted to a single stroke tablet compression machine, keeping the hardness of tablets in the range of about 4-9 kP.

Example 11 is an immediate release tablet manufactured either by dry blending or conventional wet granulation and compression process and wherefrom about 80% by weight or more of both the actives was released within about 30 minutes when tested in vitro as described above. It should be noted that the above said compositions can be also processed to get tablets by the conventional wet-granulation method known in the art. Accordingly, an aqueous solution of the binder in which the wetting agent(s) may also be included, is employed to granulate an admixture of the actives, filler and the polymer(s). The wet granulate is dried, sized, lubricated and compressed to tablets. The in vitro drug release testing procedure for the above disclosed example dosage forms is described in Example 1. The calculated release profiles of the actives from some of the representative example dosage forms are shown in Table III and FIG. 1.

TABLE III

| | Example | | | | | | | | | | | |
|---|---|---|---|---|---|---|---|---|---|---|---|---|
| | 3 | | 4 | | 5 | | 6 | | 11 | | 12 | |
| | ACTIVE | | | | | | | | | | | |
| | CP | CPM | CP | CPM | CP | CPM | CP | CPM | CP | CPM | CP | CPM | SUD |
| Mean $T_{25\%}$, hours | 0.3 | 0.3 | 0.5 | 0.5 | 1.0 | 1.0 | 1.1 | 0.9 | <0.3 | <0.3 | 0.5 | 0.4 | 0.5 |
| Mean $T_{50\%}$, hours | 0.9 | 0.9 | 1.8 | 1.9 | 3.5 | 3.3 | 4.9 | 4.3 | <0.5 | <0.5 | 1.7 | 1.8 | 1.9 |
| Mean $T_{75\%}$, hours | 1.9 | 2.0 | 3.9 | 4.0 | 7.3 | 7.1 | 11.3 | 10.1 | <0.7 | <0.7 | 3.7 | 4.0 | 4.2 |

CP = Codeine Phosphate;
CPM = Chlorpheniramine Maleate;
SUD = Pseudoephedrine

Unlike Examples 3, 5, 6 and 11, Example 4 of the invention provides optimal release for a 12 hour product. Notably, Example 4 has a ratio of total molar content of the oxyl groups in the hydrophilic polymer to the total molar content of the oxygen-containing groups in the codeine about 3.5, whereas Example 3 has the ratio less than 2.5 and Examples 5 and 6 has the ratio greater than 9.0.

The tablet dosage forms of Examples 4, 5 and 6 were evaluated for in vivo pharmacokinetic performance after a single dose administration in comparison to the IR tablet of Example 11, in 10-12 subjects. The study was carried out similar way as presented in Example 2. The Tablets of Examples 4, 5 and 6 were administered once, while the tablet of Example 11 was administered every six hours, for 12 hours (i.e. twice in 12 hours). The total dose of Codeine Phosphate was 54.3 mg in 12 hours and chlorpheniramine maleate was 8 mg. The plasma concentration of codeine and chlorpheniramine was determined by LC-MS/MS method.

Table IV shows the results of the pharmacokinetic parameters for each of the actives of Examples 4, 5 and 6 expressed as a percentage of its ratio to the corresponding parameters obtained for respective actives given as IR tablet (Example 11) every 6 hours, twice. However it is noteworthy that the IR tablet can be given as a single combination tablet (as Example 11) or as co administered single active tablets.

TABLE IV

| | EXAMPLE | | | | | |
|---|---|---|---|---|---|---|
| | 4 | | 5 | | 6 | |
| | ACTIVE | | | | | |
| | CP | CPM | CP | CPM | CP | CPM |
| Mean % $C_{max}$ (ng/ml) | 88.9 | 85.3 | 64.2 | 70.6 | 53.1 | 64.0 |
| Mean % $AUC_{0-12}$ (ng · h/ml) | 101.7 | 95.2 | 83.0 | 73.1 | 70.7 | 65.4 |
| Mean % $AUC_{inf}$ (ng · h/ml) | 104.9 | 100.5 | 112.5 | 101.6 | 110.1 | 92.7 |
| Mean % $C_{12}$ (ng/mL) | 98.6 | 85.0 | 128.6 | 74.3 | 123.1 | 61.9 |

Unlike Examples 5 and 6, Example 4 of the invention provides optimal pharmacokinetic parameters for a 12 hour product. Notably, Example 4 has a ratio of total molar content of the oxyl groups in the hydrophilic polymer to the total molar content of the oxygen-containing groups in the codeine about 3.5, whereas Examples 5 and 6 has the ratio greater than 9.0.

Example 16-32

Dosage Forms Having at Least One Tri-Oxy Active and at Least One Oxyl-Containing Non-Ionic Hydrophilic Polymer Tablet dosage forms of having the compositions as recited in Examples 16 to 32 are prepared by using the respective components shown in Tables V to VII. The tablet dosage forms are manufactured by a similar process as described for Examples 3 to 15. Tablet dosage forms of Examples 23, 24 and 25 were compressed to achieve a total Codeine Phosphate dose of 30 mg per tablet and guaifenesin to 600 mg per tablet.

TABLE V

| INGREDIENT * | EXAMPLE | | | | | | |
|---|---|---|---|---|---|---|---|
| | 16 | 17 | 18 | 19 | 20 | 21 | 22 |
| First Active (Tri-oxy active), mg [e.g. Codeine Phosphate, CP] | 30 | 30 | 30 | 30 | 30 | 30 | 20 |
| Second Active (Tri-oxy active), mg [e.g. Guaifenesin, GGE] | 600 | 600 | 600 | 600 | 600 | 600 | 400 |
| Oxyl-containing non-ionic hydrophilic polymer, mg [e.g. Hypromellose 2208] | 20 | 65 | 105 | 185 | 105 | 220 | — |
| Pharmaceutical Processing Aids, mg | 60-100 | 60-100 | 60-100 | 60-100 | 75-140 | 60-100 | 55 |
| Total Methoxyl Content of the non-ionic hydrophilic polymer (mMol.) | 0.15 | 0.49 | 0.79 | 1.39 | 0.79 | 1.65 | — |
| Total Hydroxyl Content of the non-ionic hydrophilic polymer (mMol.) | 0.11 | 0.35 | 0.57 | 1.00 | 0.57 | 1.18 | — |
| Total Oxyl Content of the non-ionic hydrophilic polymer (mMol.) | 0.26 | 0.84 | 1.35 | 2.38 | 1.35 | 2.83 | — |
| Total Molar Content of the Oxygen Containing Groups in Codeine Phosphate (mMol.) | 0.23 | 0.23 | 0.23 | 0.23 | 0.23 | 0.23 | — |
| Ratio of the total molar content of oxyl groups in the hydrophilic polymer to the total molar content of the oxygen containing groups in Codeine Phosphate | 1.15 | 3.71 | 5.96 | 10.51 | 5.96 | 12.50 | — |
| Total Molar Content of the Oxygen Containing Groups in Guaifenesin (mMol.) | 12.11 | 12.11 | 12.11 | 12.11 | 12.11 | 12.11 | — |
| Ratio of the total molar content of oxyl groups in the hydrophilic polymer to the total molar content of the oxygen containing groups in Guaifenesin | 0.02 | 0.07 | 0.11 | 0.20 | 0.11 | 0.23 | — |

* Excipients shown are exemplary of the classes; additional Pharmaceutical Processing aids known in the art can be used.

TABLE VI

| INGREDIENT * | EXAMPLE | | |
|---|---|---|---|
| | 23 % w/w | 24 % w/w | 25 % w/w |
| First Active (Tri-oxy active) [e.g. Codeine Phosphate, CP] | 3.8-3.9 | 3.2-3.7 | 3.0-3.1 |
| Second Active (Tri-oxy active) [e.g. Guaifenesin, GGE] | 76-79 | 64-74 | 59-62 |
| Oxyl-containing non-ionic hydrophilic polymer [e.g. Hypromellose 2208] | 1-5 | 8-20 | 23-26 |
| Pharmaceutical Processing Aids | 15-16 | 13-15 | 11-12 |

* Excipients shown are exemplary of the classes; additional Pharmaceutical Processing aids known in the art can be used.

The in vitro for drug release testing procedure for the above example dosage forms is described in Example 1. The calculated release profiles of the actives from some of the representative examples are shown in Table VIII and FIG. II. Example 22 is an immediate release tablet wherefrom about 80% by weight or more of both the actives was released within about 30 minutes when tested in vitro as previously described.

TABLE VIII

| | EXAMPLE | | | | | | | | | |
|---|---|---|---|---|---|---|---|---|---|---|
| | 16 | | 17 | | 18 | | 19 | | 22 | |
| | ACTIVE | | | | | | | | | |
| | GGE | CP | GGE | CP | GGE | CP | GGE | CP | GGE | CP |
| Mean $T_{25\%}$, hours | 0.20 | 0.30 | 0.5 | 0.3 | 0.8 | 0.6 | 1.4 | 0.9 | <0.3 | <0.3 |

TABLE VII

| INGREDIENT * | EXAMPLE | | | | | | |
|---|---|---|---|---|---|---|---|
| | 26 (mg) | 27 (mg) | 28 (mg) | 29 (mg) | 30 (mg) | 31 (mg) | 32 (mg) |
| First Active (Tri-oxy active) [e.g. Codeine Phosphate, CP] | 30 | 30 | 30 | 30 | 30 | 30 | 30 |
| Second Active (Tri-oxy active) [e.g. Guaifenesin, GGE] | 600 | 600 | 600 | 600 | 600 | — | — |
| Second Active (Non-oxo active) [e.g. Dextromethorphan, DXM] | — | — | — | — | — | 30 | — |
| Third Active [e.g. Pseudoephedrine, SUD] | — | — | — | — | 60 | — | 60 |
| Third Active [e.g. Phenylephrine, PE] | — | — | — | 15-30 | — | 15-30 | — |
| Oxyl-containing non-ionic hydrophilic polymer [e.g. Hypromellose 2208] | 53 | 25 | — | 60-125 | 80-150 | 60-150 | 80-150 |
| Oxyl-containing non-ionic hydrophilic polymer [e.g. Hypromellose 2910] | 40 | 10 | 80 | — | — | — | — |
| Pharmaceutical Processing Aids | 70-145 | 80-125 | 90-120 | 90-120 | 90-120 | 90-120 | 90-120 |

* Excipients shown are exemplary of the classes; additional Pharmaceutical Processing aids known in the art can be used.

TABLE VIII-continued

| | EXAMPLE | | | | | | | | | |
|---|---|---|---|---|---|---|---|---|---|---|
| | 16 | | 17 | | 18 | | 19 | | 22 | |
| | | | | | ACTIVE | | | | | |
| | GGE | CP | GGE | CP | GGE | CP | GGE | CP | GGE | CP |
| Mean $T_{50\%}$, hours | 0.70 | 0.80 | 2.2 | 1.9 | 3.0 | 2.4 | 4.4 | 3.3 | <0.5 | <0.5 |
| Mean $T_{75\%}$, hours, | 1.40 | 1.50 | 5.2 | 4.8 | 6.5 | 5.6 | 8.9 | 7.0 | <0.7 | <0.7 |

GGE = guaifenesin;
CP = codeine phosphate

Unlike Examples 16 and 19, Examples 17 and 18 of the invention provides optimal release for a 12 hour product. Notably, Examples 17 and 18 have a ratio of total molar content of the oxyl groups in the hydrophilic polymer to the total molar content of the oxygen-containing groups in the guaifenesin is between 0.07 about 0.18, whereas Example 16 has the ratio less than 0.07 and Example 19 has the ratio greater than 0.18. The tablet dosage forms of Examples 17, 18 and 19 were evaluated for in vivo pharmacokinetic performance after a single dose administration in comparison to the IR tablet of Example 22, in 10-12 subjects. The study was carried out in similar way as outlined in Example 2. In particular, the dosage forms of Example 17, 18 and 19 were administered once, while the dosage form of Example 22 was administered every four hours, for 12 hours. (i.e. three times in 12 hours). The total dose of guaifenesin was 1200 mg in 12 hours and codeine phosphate was 60 mg in 12 hours. The plasma concentration of GGE and codeine were determined by LC-MS/MS method Table VIII shows the results of the pharmacokinetic parameters for each of the actives of Examples 17, 18 and 19 expressed as a percentage of its ratio to the corresponding parameters obtained for respective actives given as IR tablet (Example 22) every 4 hours for 12 hours. The mean $T_{max}$ is expressed as absolute value in hours for each active from respective examples. However it is noteworthy that the IR tablet can be given as a single combination tablet (as Example 22) or as co administered single active tablets.

TABLE IX

| | EXAMPLE | | | | | |
|---|---|---|---|---|---|---|
| | 17 | | 18 | | 19 | |
| | GGE | CP | GGE | CP | GGE | CP |
| Mean % $C_{max}$ (ng/ml) | 75.4 | 100.2 | 60.0 | 90.8 | 44.7 | 80.0 |
| Mean % $AUC_{0-12}$ (ng · h/ml) | 91.7 | 97.3 | 89.8 | 98.1 | 86.3 | 99.8 |
| Mean % AUC 0-α (ng · h/ml) | 91.4 | 97.3 | 89.8 | 99.2 | 92.0 | 106.1 |
| Mean % $C_{12}$ (ng/mL) | 29.3 | 50.5 | 71.2 | 62.5 | 111 | 68.4 |
| Mean $T_{max}$ (hour) | 2.0 | 4.0 | 2.0 | 4.0 | 2.0 | 4.0 |

It can be seen from Examples 17, 18 and 19, the criticality of the type and the minimum and maximum levels of the non-ionic oxyl-containing hydrophilic polymer that is essential for enabling a product for delivery once every 12 hours, for oxo-actives such as guaifenesin and codeine. Notably, Examples 17 and 18 have a ratio of total molar content of the oxyl groups in the hydrophilic polymer to the total molar content of the oxygen-containing groups in the guaifenesin is between 0.07 about 0.18, whereas Example 19 has the ratio greater than 0.18. Furthermore, Table X gives the absolute $C_{max}$ and $C_{min}$ value of the dosage forms of invention upon steady state simulation. For the purpose of simulations, dosage forms of Examples 17 are 18 are administered two tablets every 12 hours.

TABLE X

| | EXAMPLE | | | |
|---|---|---|---|---|
| | 17 | | 18 | |
| ACTIVE | GGE | CP | GGE | CP |
| Mean $C_{max}$ (ng/mL) | 1342 | 59.2 | 1153 | 56.9 |
| Mean $C_{minss}$ (ng/mL) | 56 | 15.7 | 136 | 19.8 |

Examples 17 and 18 of the invention provides optimal pharmacokinetic for a 12 hour product.

Examples 33-48

Dosage Forms Having at Least One Tri-Oxy Active and at Least One Oxyl-Containing Non-Ionic Hydrophilic Polymer Tablet dosage forms of having the compositions as recited in Examples 27 through 38 are prepared by using the respective components shown in Tables XI to XIII. The in vitro for drug release testing procedure for the said example dosage forms is described in Example 1. The release profiles of the actives from some of the representative examples are shown in Table-XIV and FIG. III. Examples 38 and 39 are immediate release tablets of hydrocodone bitartrate (HB) and GGE respectively and which release about 80% by weight or more of the active within about 30 minutes when tested in vitro as previously described.

Example 38 is a commercially available hydrocodone bitartrate IR tablet (e.g. Hycodan®, Endo Pharmaceuticals) and it contains an additional active homatropin methyl bromide. IR Tablets of guaifenesin and hydrocodone bitartrate (Examples 38 and 39, respectively) together constitute as reference product for comparison of the said example dosage forms of the current invention.

TABLE XI

| | EXAMPLE | | | | | | |
|---|---|---|---|---|---|---|---|
| INGREDIENT* | 33 | 34 | 35 | 36 | 37 | 38[#] | 39 |
| First Active (Tri-oxy active), mg [e.g. Guaifenesin, GGE] | 600 | 600 | 600 | 600 | 600 | — | 400 |
| First Active (Tri-oxy active), mg [e.g. Hydrocodone Bitartrate, HB] | 5 | 5 | 5 | 5 | 5 | 5 | — |

TABLE XI-continued

| INGREDIENT* | EXAMPLE | | | | | | |
|---|---|---|---|---|---|---|---|
| | 33 | 34 | 35 | 36 | 37 | 38# | 39 |
| Homatropine Methylbromide, mg | — | — | — | — | — | 1.5 | — |
| Oxyl-containing non-ionic hydrophilic polymer, mg [e.g. Hypromellose 2208] | 25 | 65 | 145 | 185 | 105 | — | — |
| Pharmaceutical Processing Aids, mg | 45 | 40-65 | 40-65 | 40-65 | 50-120 | 50-150 | 50-70 |
| Total Methoxyl Content of the non-ionic hydrophilic polymer (mMol.) | 0.19 | 0.49 | 1.09 | 1.39 | 0.79 | — | — |
| Total Hydroxyl Content of the non-ionic hydrophilic polymer (mMol.) | 0.13 | 0.35 | 0.78 | 1.00 | 0.57 | — | — |
| Total Oxyl Content of the non-ionic hydrophilic polymer (mMol.) | 0.32 | 0.84 | 1.87 | 2.38 | 1.35 | — | — |
| Total Molar Content of the Oxygen Containing Groups in Guaifenesin (mMol.) | 12.11 | 12.11 | 12.11 | 12.11 | 12.11 | — | — |
| Ratio of the total molar content of oxyl groups in the hydrophilic polymer to the total molar content of the oxygen containing groups in Guaifenesin | 0.03 | 0.07 | 0.15 | 0.20 | 0.11 | — | — |

*Excipients shown are exemplary of the classes; additional Pharmaceutical Processing aids known in the art can be used.
Commercially available hydrocodone bitartrate IR tablet (e.g. Hycodan ®)

TABLE XII

| INGREDIENT * | EXAMPLE | | |
|---|---|---|---|
| | 40 % w/w | 41 % w/w | 42 % w/w |
| First Active (Tri-oxy active) [e.g. Guaifenesin, GGE] | 78-82 | 66-76 | 62-63 |
| First Active (Tri-oxy active) [e.g. Hydrocodone Bitartrate, HB] | 0.7 | 0.5-0.6 | 0.5 |
| Oxyl-containing non-ionic hydrophilic polymer [e.g. Hypromellose 2208] | 1-5 | 8-20 | 23-27 |
| Pharmaceutical Processing Aids | 16 | 13-15 | 11-13 |

* Excipients shown are exemplary of the classes; additional Pharmaceutical Processing aids known in the art can be used.

TABLE XIV

| | Example | | | | | | | | | |
|---|---|---|---|---|---|---|---|---|---|---|
| | 33 | | 34 | | 35 ACTIVE | | 36 | | 38 | 39 |
| | GGE | HB | GGE | HB | GGE | HB | GGE | HB | HB | GGE |
| Mean $T_{25\%}$, hours | 0.2 | 0.3 | 0.6 | 0.5 | 1.0 | 1.0 | 1.3 | 1.3 | <0.3 | <0.3 |
| Mean $T_{50\%}$, hours | 0.6 | 0.7 | 1.9 | 1.5 | 3.1 | 2.9 | 4.0 | 4.1 | <0.5 | <0.5 |
| Mean $T_{75\%}$, hours, | 1.4 | 1.4 | 4.0 | 3.3 | 6.3 | 5.6 | 7.5 | 7.3 | <0.7 | <0.7 |

GGE = guaifenesin;
HB = hydrocodone bitartrate

TABLE XIII

| INGREDIENT * | EXAMPLE | | | | | |
|---|---|---|---|---|---|---|
| | 43 (mg) | 44 (mg) | 45 (mg) | 46 (mg) | 47 (mg) | 48 (mg) |
| First Active (Tri-oxy active) [e.g. Guaifenesin, GGE] | 600 | 600 | 190 | 600 | 600 | 600 |
| First Active (Tri-oxy active) [e.g. Hydrocodone Bitartrate, HB] | 5 | 5 | — | 5 | 5 | 5 |
| Second Active (Non Oxo Containing) (e.g. Dextromethorphan) | — | — | — | 30 | — | 30 |
| Third Active [e.g. Pseudoephedrine, SUD] | — | — | — | 60 | — | — |
| Third Active [e.g. Phenylephrine, PE] | — | — | — | — | 15-30 | 15-30 |
| Oxyl-containing non-ionic hydrophilic polymer [e.g. Hypromellose 2208] | 73 | — | — | 80-150 | 80-150 | 80-150 |
| Oxyl-containing non-ionic hydrophilic polymer [e.g. Hypromellose 2910] | 55 | 110 | — | — | — | — |
| Pharmaceutical Processing Aids | 90-120 | 40-65 | 90-120 | 50-120 | 50-120 | 50-120 |

* Excipients shown are exemplary of the classes; additional tableting aids known in the art can be used.

Unlike Examples 33, 36, 38 and 39, Examples 34 and 35 of the invention provides optimal release for a 12 hour product. Notably, Examples 34 and 35 have a ratio of total molar content of the oxyl groups in the hydrophilic polymer to the total molar content of the oxygen-containing groups in the guaifenesin is between 0.07 about 0.18, whereas Example 33 has the ratio less than 0.07 and Example 36 has the ratio greater than 0.18

The tablet dosage forms of Examples 33, 34 and 35 were evaluated for in vivo pharmacokinetic performance after a single dose administration in comparison to the Guaifenesin IR tablet(s) of Example 39 and hydrocodone bitartrate IR tablet (e.g. Hycodan®, Example 38), in 10-12 subjects. The study was carried out as outlined in Example 2. Specifically, the dosage forms of Examples 33, 34 and 35 were administered once, while Guaifenesin IR tablet was given every four hours for 12 hours, and the hydrocodone bitartrate IR reference tablet given every six hours for 12 hours. The total dose of Guaifenesin was 1200 mg in 12 hours and of hydrocodone bitartrate was 10 mg in 12 hours. The plasma concentration of GGE and hydrocodone were determined by LC-MS/MS method.

Table XV shows the results of the pharmacokinetic parameters for each of the actives of Examples 33, 34 and 35 expressed as a percentage of its ratio to the corresponding parameters obtained for respective actives given as IR tablets (Examples 31 and 32 every four hours and every 6 hours respectively, for 12 hours. The absolute minimum plasma concentrations at steady state for guaifenesin and hydrocodone from the administered dosage forms of some examples of this invention are shown in Table XVI.

TABLE XV

| | EXAMPLE | | | | | |
|---|---|---|---|---|---|---|
| | 33 | | 34 | | 35 | |
| | ACTIVE | | | | | |
| | GGE | HB | GGE | HB | GGE | HB |
| Mean % $C_{max}$ (ng/ml) | 75.4 | 100.2 | 60.0 | 90.8 | 44.7 | 80.0 |
| Mean % $AUC_{0-12}$ (ng · h/ml) | 95.3 | 108.0 | 90.3 | 102.9 | 74.1 | 94.9 |
| Mean % $AUC_{inf}$ (ng · h/ml) | 91.4 | 97.3 | 89.8 | 99.2 | 92.0 | 106.1 |
| Mean % $C_{12}$ (ng/mL) | 30.2 | 50.7 | 70.8 | 63.6 | 87.2 | 67.5 |
| Mean $T_{max}$(h) | 1.3 | 2.8 | 2.0 | 4.0 | 2.0 | 4.0 |

Unlike Example 33, Examples 34 and 35 of the invention provides optimal pharmacokinetic for a product formulated for delivery once every 12 hours. Notably, Examples 34 and 35 have a ratio of total molar content of the oxyl groups in the hydrophilic polymer to the total molar content of the oxygen-containing groups in the guaifenesin is between 0.07 about 0.18, whereas Example 33 has the ratio less than 0.07

TABLE XVI

| | EXAMPLE | | |
|---|---|---|---|
| ACTIVE | 33 GGE | 34 GGE | 35 GGE |
| Mean $C_{minss}$ (ng/mL) | 1.85 | 14.1 | 22.8 |

As it can be seen from Examples 34 and 35 have acceptable Mean $C_{minss}$ (ng/mL) value of greater than 3 ng/mL for 12 hour product.

Example 49

Coated Pharmaceutical Tablets

The tablet dosage forms of Examples 3 to 10, 12 to 15, 16-21, 23-32, 33-37 and 40 to 48 can be further coated with a coating solution having typical composition set forth in Table XVII, using conventional tablet coating procedures known in the art to a weight gain of about 2 to 6%.

TABLE XVII

| INGREDIENT * | Composition in % w/w |
|---|---|
| Film coating polymer (e.g. Methocel E 5) | 8.0 |
| Plasticizer (e.g. Polyethylene glycol, NF 8000) | 0.6 |
| Coating Solvent (e.g. Ethanol) | 54.8 |
| Coating Solvent Water | 36.6 |

* Excipients shown are exemplary of the classes; additional pharmaceutical processing aids known in the art can be used.

Examples 50-51

In Vitro Release of Actives from Exemplary Embodiments

Tablet dosage forms of having combination of the oxo-actives (e.g. guaifenesin, codeine phosphate etc.) in the compositions as recited in Examples 50 and 51 are prepared by using the respective components shown in Tables XVIII. The in vitro drug release testing procedure for the said example dosage forms is described in Example 1. The release profiles of the actives from some of the representative formulations are shown in Table-XIX. Example 50 contains the oxyl-containing non-ionic hydrophilic polymer within the range disclosed in the invention, while Example 51 does not contain polymer within the range disclosed in the invention.

TABLE XVIII

| | EXAMPLE | |
|---|---|---|
| INGREDIENT * | 50 (mg) | 51 (mg) |
| First Active (Tri-oxy active) [e.g. Codeine Phosphate, CP] | 30 | 30 |
| Second Active (Tri-oxy active) [e.g. Guaifenesin, GGE] | 600 | 600 |
| Oxyl-containing non-ionic hydrophilic polymer [e.g. Hypromellose 2208] | 105 | — |
| Oxyl-containing non-ionic hydrophilic polymer [e.g. Hypromellose 2910] | — | 15 |
| Pharmaceutical Processing Aids | 65-100 | 65-105 |

* Excipients shown are exemplary of the classes; additional Pharmaceutical Processing aids known in the art can be used.

TABLE XIX

| | Example | | | |
|---|---|---|---|---|
| | 50 | | 51 | |
| | GGE | CP | GGE | CP |
| Mean $T_{25\%}$, hours | 0.84 | 0.55 | 1.00 | 0.85 |
| Mean $T_{50\%}$, hours | 3.01 | 2.40 | 3.90 | 3.60 |
| Mean $T_{75\%}$, hours, | 6.51 | 5.57 | 8.00 | 7.12 |

Unlike Example 51, Example 50 of the invention provides optimal release for a 12 hour product. The tablet dosage forms of Examples 50 and 51 were evaluated for in vivo pharmacokinetic performance after a single dose administration of two (2) tablets each. Table XX shows the absolute values of the pharmacokinetic parameters for guaifenesin.

TABLE XX

|  | EXAMPLE | |
| --- | --- | --- |
|  | 50 GGE | 51 GGE |
| Mean $C_{max}$ (ng/ml) | 1050 | 821 |

Unlike Example 51, Example 50 of the invention provides greater $C_{max}$ for a 12 hour product.

Example 52

Food Effect Pharmacokinetics

The tablet dosage forms of Example 18, the IR tablets of Example 22 were evaluated for Effect of food on in vivo pharmacokinetic performance after a single dose administration to 10 subjects. Accordingly, the tablet of Example 18 (Test formulation) administered either after overnight fasting or within 30 minutes of administration of food. Similarly, in another group, the IR tablets of Example 22 (Reference formulation) were given either after overnight fasting or within 30 minutes of administration of food. The plasma analysis for guaifenesin and codeine were carried out by LC-MS/MS. The PK parameters are expressed as a ratio to the corresponding parameters obtained for each dosage form after administration with food or under fasted state.

It was observed that a there was no significant food effect seen for guaifenesin and codeine from the Example 18 tablets. On the contrary, the IR tablets exhibited a significant food effect wherein, the plasma guaifenesin $C_{max}$ was significantly low when administered with food compared to when given under fasted conditions, as shown in the Table XXI & XXII wherein the ratios of the fed-to-fasted PK results for guaifenesin are given.

TABLE XXI

|  | Example 18 | | Example 22 |
| --- | --- | --- | --- |
| ACTIVE | GGE | CP | GGE |
| Mean % $C_{max}$ ratio (fed/fasted) (ng/ml) | 102 | 127 | 67 |
| Mean % AUC $_{last}$ ratio (fed/fasted) (ng · h/ml) | 98 | 109 | 89 |
| Mean % AUC $_{0-\alpha}$ ratio (fed/fasted) (ng · h/ml) | 96 | 104 | 89 |

Unlike the Example 22, Example 18, containing appropriate level of oxyl-containing non-ionic hydrophilic polymer, is less sensitive to food effect.

Example 53-54

Effect of Oxyl-Containing Non-Ionic Polymer in Comparison to Ionic Polymer on Food Effect Pharmacokinetic Study Tablet dosage forms according to the current invention having combination of oxo-actives (e.g. guaifenesin and Codeine phosphate) in the compositions as recited in Examples 53 and 54 shown in Table XIX were evaluated for food effect pharmacokinetics on similar lines as described under Example 52. While dosage form of Example 53 contains only oxyl-containing non-ionic hydrophilic polymer within the range disclosed in the invention, the Example 54 has ionic hydrophilic polymer along with oxyl-containing non-ionic hydrophilic polymer.

TABLE XXII

|  | EXAMPLE | |
| --- | --- | --- |
| Ingredient* | 53 (mg) | 54 (mg) |
| First Active (Tri-oxy active) [e.g. Codeine Phosphate, CP] | 30 | 30 |
| Second Active (Tri-oxy active) [e.g. Guaifenesin, GGE] | 600 | 600 |
| Oxyl-containing non-ionic hydrophilic polymer [e.g. Hypromellose 2208 or Hypromellose 2910] | 105 | 15 |
| Ionic Hydrophilic Polymer [e.g. Carbopol 974P] | — | 7.5 |
| Pharmaceutical Processing Aids | 75-120 | 65-85 |

*Excipients shown are exemplary of the classes; additional Pharmaceutical Processing aids known in the art can be used.

The dosage form of Example 53 showed no food effect on $C_{max}$, $AUC_{0-inf}$. On the contrary, the ionic polymer containing formulation similar to Example 54 is prone to food effect, probably due to the ionic nature of the polymer, which is known to be sensitive to pH changes in the presence of food.

The invention claimed is:

1. A solid matrix tablet pharmaceutical composition consisting essentially of a monolithic extended release matrix having:
    54 mg of codeine phosphate;
    8 mg chlorpheniramine maleate;
    60 to 125 mg of hydroxypropyl methylcellulose;
    and one or more pharmaceutical processing aids, wherein the codeine phosphate and chlorpheniramine maleate are present as a homogenous admixture within the matrix.

2. The pharmaceutical composition of claim 1 wherein the hydroxypropyl methylcellulose is Hypromellose 2208 and is present in an amount of from 65 mg to 85 mg.

3. The pharmaceutical composition of claim 1 that has a release time of 25% of codeine and chlorpheniramine of from between 0.3 hours and 1.0 hours, a 50% release time of codeine and chlorpheniramine of from between 0.9 hours and 4.9 hours or a 75% release time of codeine and chlorpheniramine of from between 2.0 hours and 11.3 hours determined using a USP Type II (paddle) Dissolution Apparatus set at 50 rpm in about 900 mL of 0.1 N hydrochloric acid solution in water at about 37° C.

4. An extended release monolithic solid matrix tablet pharmaceutical composition comprising 54 mg of codeine phosphate; 8 mg chlorpheniramine maleate; and a 60 mg to 125 mg release rate controlling non-ionic oxyl-containing hydrophilic polymer wherein the codeine phosphate and chlorpheniramine maleate are present as a homogenous admixture within the matrix.

5. The pharmaceutical composition of claim 4 having from 65 mg to 85 mg of a release rate controlling non-ionic oxyl-containing hydrophilic polymer which is hydroxypropyl methylcellulose.

6. The pharmaceutical composition of claim 4 that has a release time of 25% of codeine phosphate and chlorpheniramine maleate of from between 0.3 hours and 1.0 hours, a 50% release time of codeine phosphate and chlorpheniramine maleate of from between 0.9 hours and 4.9 hours or a 75% release time of codeine phosphate and chlorpheniramine maleate of from between 2.0 hours and 11.3 hours determined using a USP Type II (paddle) Dissolution Apparatus set at 50 rpm in about 900 mL of 0.1 N hydrochloric acid solution in water at about 37° C.

7. The pharmaceutical composition of claim 4 which when placed in a USP Type II (paddle) Dissolution Apparatus at 50 rpm in 900 mL of 0.1 N hydrochloric acid solution in water at 37° C. about 50% of the codeine phosphate is released between 1.5 hours to 3 hours.

8. A single layer solid matrix tablet pharmaceutical composition comprising: codeine or a pharmaceutically acceptable salt thereof; chlorpheniramine or a pharmaceutically acceptable salt thereof; and 60 mg to 125 mg of a release rate controlling non-ionic oxyl containing polymer and said composition substantially free of ionic polymer which when placed in a USP Type II Dissolution Apparatus at 50 rpm in 900 mL of 0.1 N hydrochloric acid solution in water at 37° C. about 50% of the codeine or pharmaceutically acceptable salt is released between 1.5 hours to 3 hours, wherein the codeine and chlorpheniramine are present as a homogenous admixture within the matrix.

9. The pharmaceutical composition of claim 8 which when placed in a USP Type II Dissolution Apparatus at 50 rpm in 900 mL of 0.1 N hydrochloric acid solution in water at 37° C. the ratio of the amount of codeine or pharmaceutically acceptable salt thereof released to the amount of chlorpheniramine or pharmaceutically acceptable salt thereof released at a single time point between 1 hour and 4 hours is from about 0.8:1 and about 1.2:1.

10. The pharmaceutical composition of claim 8 wherein the release rate controlling non-ionic oxyl containing polymer is hydroxypropyl methylcellulose.

11. The pharmaceutical composition of claim 8 said codeine or pharmaceutically acceptable is 54 mg of codeine phosphate; said chlorpheniramine or pharmaceutically acceptable thereof is 8 mg of chlorpheniramine maleate; or said release rate controlling non-ionic oxyl containing polymer is hydroxypropyl methylcellulose which is present in an amount of from 65 mg to 85 mg.

12. The pharmaceutical composition of claim 8 said codeine or pharmaceutically acceptable salt thereof is 54 mg of codeine phosphate.

13. The pharmaceutical composition of claim 8 said chlorpheniramine or pharmaceutically acceptable salt thereof is 8 mg of chlorpheniramine maleate.

14. A single layer tablet consisting of:
(a) a first active agent which is codeine or a pharmaceutically acceptable salt thereof;
(b) a second active agent which is chlorpheniramine or a pharmaceutically acceptable salt thereof;
(c) a release rate controlling non-ionic oxyl-containing hydrophilic polymer; and
(d) one or more pharmaceutical processing aids,
said single layer tablet when placed in a USP Type II Dissolution Apparatus at 50 rpm in 900 mL of 0.1 N hydrochloric acid solution in water at 37° C. about 50% of the codeine or pharmaceutically acceptable salt is released between 1.5 hours to 3 hours and said first active agent, said second active agent and said release rate controlling non-ionic oxyl-containing hydrophilic polymer are present in amounts to provide therapeutically effective amounts of said first active agent and said second active agent sufficient for dosing to a human subject once every 12 hours wherein said first active agent and said second active agent are in a homogenous admixture within said single layer tablet.

15. The single layer tablet of claim 14 said first active agent is 54 mg of codeine phosphate.

16. The single layer tablet of claim 14 said second active agent is 8 mg of chlorpheniramine maleate.

17. The single layer tablet of claim 14 wherein said release rate controlling non-ionic oxyl-containing hydrophilic polymer is hydroxypropyl methylcellulose which is present in an amount of from 60 mg to 125 mg.

18. The single layer tablet of claim 14 wherein the release rate controlling non-ionic oxyl-containing hydrophilic polymer is hydroxypropyl methylcellulose which is present in an amount of from 65 mg to 85 mg.

19. The single layer tablet of claim 14 which is substantially free of ionic polymer.

20. The single layer tablet of claim 14 wherein the hydroxypropyl methylcellulose has an average apparent viscosity of about 3000 cP to about 15000 cP when determined in a 2% solution in water at 20° C.

21. The single layer tablet of claim 14 that has no food effect when administered to a human subject.

22. The single layer tablet of claim 14 which is resistant to alcohol associated dose dumping.

* * * * *